United States Patent
Tribus

(10) Patent No.: US 8,430,929 B2
(45) Date of Patent: Apr. 30, 2013

(54) SPINE REDUCTION AND STABILIZATION DEVICE

(76) Inventor: Clifford Tribus, Madison, WI (US)

(*) Notice: Subject to any disclaimer, the term of this patent is extended or adjusted under 35 U.S.C. 154(b) by 1167 days.

(21) Appl. No.: 11/621,834

(22) Filed: Jan. 10, 2007

(65) Prior Publication Data

US 2008/0015694 A1    Jan. 17, 2008

Related U.S. Application Data

(60) Provisional application No. 60/759,105, filed on Jan. 13, 2006.

(51) Int. Cl.
*A61B 17/58* (2006.01)

(52) U.S. Cl.
USPC .......................................... 623/17.11

(58) Field of Classification Search .... 623/17.11–17.16; 606/79–85, 86 R, 87–89, 280–299
See application file for complete search history.

(56) References Cited

U.S. PATENT DOCUMENTS

| | | | |
|---|---|---|---|
| 4,401,112 A | 8/1983 | Rezaian | |
| 4,611,581 A | 9/1986 | Stefee | |
| 4,743,256 A | 5/1988 | Brantigan | |
| 4,759,709 A | 7/1988 | Luken, Jr. et al. | |
| 5,062,850 A | 11/1991 | MacMillan et al. | |
| 5,217,497 A | 6/1993 | Mehdian | |
| 5,258,031 A | 11/1993 | Salib et al. | |
| 5,306,309 A * | 4/1994 | Wagner et al. | 623/17.16 |
| 5,314,477 A | 5/1994 | Marnay | |
| 5,423,826 A * | 6/1995 | Coates et al. | 606/96 |
| 5,458,641 A * | 10/1995 | Ramirez Jimenez | 623/17.11 |
| 5,458,642 A | 10/1995 | Beer et al. | |
| 5,505,732 A * | 4/1996 | Michelson | 606/86 A |
| 5,522,899 A | 6/1996 | Michelson | |
| 5,554,191 A | 9/1996 | Lahille et al. | |
| 5,562,738 A | 10/1996 | Boyd et al. | |
| 5,645,599 A | 7/1997 | Samani | |
| 5,653,763 A | 8/1997 | Errico et al. | |
| 5,674,296 A | 10/1997 | Bryan et al. | |
| 5,679,296 A | 10/1997 | Kelman et al. | |
| 5,713,899 A | 2/1998 | Marney et al. | |
| 5,722,977 A * | 3/1998 | Wilhelmy | 606/84 |
| 5,766,252 A | 6/1998 | Henry et al. | |
| 5,779,707 A | 7/1998 | Bertholet et al. | |
| 5,782,831 A | 7/1998 | Sherman et al. | |
| 5,800,433 A | 9/1998 | Benzel et al. | |
| 5,814,046 A | 9/1998 | Hopf | |
| 5,885,299 A | 3/1999 | Winslow et al. | |

(Continued)

OTHER PUBLICATIONS

ESM Technologies, LLC website, http://www.esmtech.com, printed Apr. 13, 2007; earliest available date: Feb. 2006.

*Primary Examiner* — Kevin T Truong
*Assistant Examiner* — Christopher Beccia
(74) *Attorney, Agent, or Firm* — Foley & Lardner LLP

(57) ABSTRACT

A spine stabilization device is placed between adjacent vertebral bodies of the vertebrae of a spine to effect a reduction and to support the adjacent vertebral bodies for fusion at the desired alignment and spacing. The stabilization device includes a first plate adapted for fixation to one of the adjacent vertebral bodies, a second plate adapted for fixation to the other, or both, of the adjacent vertebral bodies, an adjustable connector connecting the first and second plates and an intervertebral body attached to the second plate and having an intervertebral extension adapted for insertion between the adjacent vertebral bodies.

18 Claims, 21 Drawing Sheets

U.S. PATENT DOCUMENTS

| | | | |
|---|---|---|---|
| 5,888,223 A | 3/1999 | Bray, Jr. | |
| 5,895,428 A | 4/1999 | Berry | |
| 5,899,901 A | 5/1999 | Middleton | |
| 6,106,557 A * | 8/2000 | Robioneck et al. | 623/17.15 |
| 6,156,037 A * | 12/2000 | LeHuec et al. | 606/247 |
| 6,159,214 A * | 12/2000 | Michelson | 606/80 |
| 6,159,244 A * | 12/2000 | Suddaby | 623/17.11 |
| 6,224,599 B1 * | 5/2001 | Baynham et al. | 606/90 |
| 6,228,085 B1 | 5/2001 | Theken et al. | |
| 6,461,359 B1 * | 10/2002 | Tribus et al. | 606/247 |
| 6,468,309 B1 * | 10/2002 | Lieberman | 623/17.11 |
| 6,506,151 B2 * | 1/2003 | Estes et al. | 600/226 |
| 6,540,785 B1 * | 4/2003 | Gill et al. | 623/17.14 |
| RE38,684 E * | 1/2005 | Cesarone | 606/915 |
| 6,884,242 B2 | 4/2005 | LeHuec et al. | |
| 6,989,012 B2 | 1/2006 | LeHuec et al. | |
| 7,022,138 B2 * | 4/2006 | Mashburn | 623/17.13 |
| 7,066,960 B1 | 6/2006 | Dickman | |
| 7,153,303 B2 * | 12/2006 | Squires et al. | 606/79 |
| 7,186,256 B2 * | 3/2007 | Michelson | 606/71 |
| 7,320,708 B1 * | 1/2008 | Bernstein | 623/17.15 |
| 7,473,255 B2 * | 1/2009 | McGarity et al. | 606/86 B |
| 7,547,308 B2 * | 6/2009 | Bertagnoli et al. | 606/90 |
| 7,632,282 B2 * | 12/2009 | Dinville | 606/99 |
| 7,635,389 B2 * | 12/2009 | Yu et al. | 623/17.15 |
| 7,674,292 B2 * | 3/2010 | Zubok et al. | 623/17.11 |
| 7,794,465 B2 * | 9/2010 | Marik et al. | 606/87 |
| 2005/0059976 A1 * | 3/2005 | Bryan et al. | 606/80 |
| 2005/0148839 A1 | 7/2005 | Shechtman et al. | |
| 2006/0074420 A1 | 4/2006 | LeHuec et al. | |
| 2006/0195089 A1 | 8/2006 | LeHuec et al. | |
| 2007/0016302 A1 | 1/2007 | Dickman | |
| 2008/0215153 A1 * | 9/2008 | Butterman et al. | 623/17.16 |
| 2008/0234686 A1 * | 9/2008 | Beaurain et al. | 606/90 |

* cited by examiner

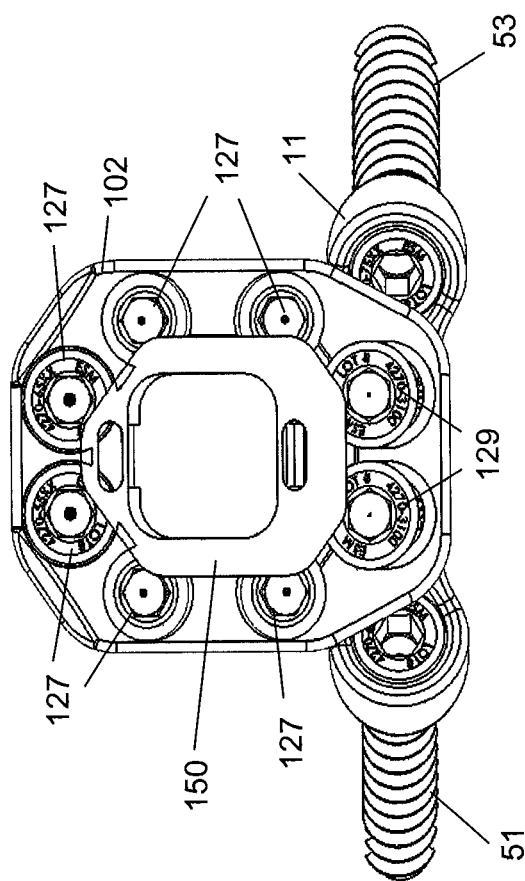

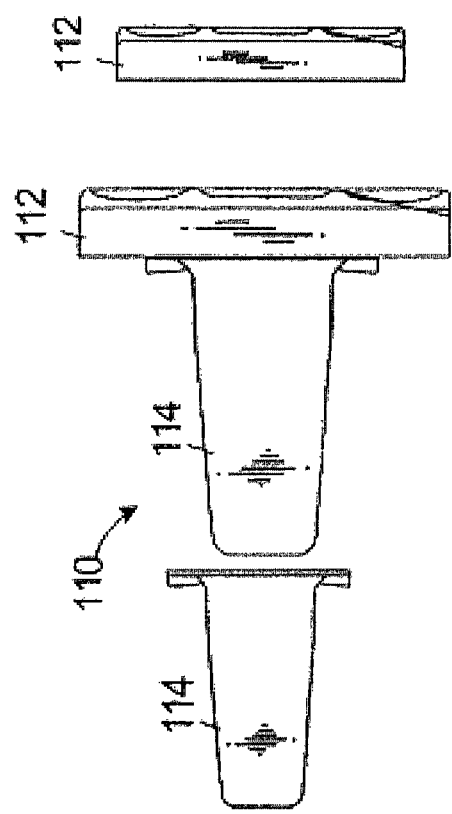

SPINE REDUCTION AND STABILIZATION DEVICE

CROSS-REFERENCE TO RELATED APPLICATION

This application claims priority to U.S. Provisional Application No. 60/759,105, filed Jan. 13, 2006, the entire disclosure of which is incorporated herein by reference.

FIELD

The present invention relates generally to the reduction and stabilization of vertebral bodies in the spinal column, as well as methods and instruments for achieving the same.

BACKGROUND

The spinal column of humans provides support for the body and protection to the delicate spinal cord and nerves. The spinal column comprises a series of vertebrae stacked on top of each other. Each vertebra has a relatively large vertebral body located in the anterior portion of the spine and provides the majority of the weight-bearing support of the vertebral column. Each vertebral body has relatively strong bone comprising the outside surface of the body (cortical) and relatively weak bone comprising the center of the body (cancellous). Situated between each vertebral body is an intervertebral disc, which provides for cushioning and dampening of compressive forces to the spinal column. Located just posterior to the vertebral body and intervertebral disc is the spinal canal containing the delicate spinal cord and nerves. Posterior to the spinal canal are the different articulating processes of the vertebrae.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, tumors, and the like. Patients that suffer from such conditions usually experience extreme and debilitating pain and often neurologic deficit.

Spinal fusion is a technique often utilizing surgical implants which mechanically immobilize areas of the spine with eventual incorporation of grafting material. Such techniques have been used effectively to treat the above-described conditions and, in most cases, to relieve pain suffered by the patient. However, there are some disadvantages to the present fixation devices.

One technique for spinal fixation includes immobilization of the spine by the use of spine rods that run generally parallel to the spine. In practicing this technique, the posterior surface of the spine is exposed, and bone screws are first fastened to the pedicles of the appropriate vertebrae or to the sacrum, acting as anchor points for the spine rods. The bone screws are generally placed two per vertebrae, one at each pedicle on either side of the spinous process. Clamp assemblies join the spine rods to the screws. The spine rods are generally bent to achieve the desired curvature of the spinal column. Such systems are very stable but require implanting screws into each vertebrae to be treated. Also, since the pedicles of vertebrae above the second lumbar vertebra (L-2) are very small, only small bone screws can be used, which sometimes do not give the needed support to stabilize the spine. To stabilize the unstable spine sufficiently, one to two vertebrae above and one to two vertebrae below the area to be treated are often used for implanting the screws. The rods and clamps are surgically fixed to the spine from a posterior approach.

Anterior fixation devices have also been used, such as anterior plate systems. One type of anterior plate system involves a titanium plate with unicortical titanium bone screws that may lock to the plate and are placed over the anterior surface of the vertebral body. Another type of anterolateral plate system uses bicortical screws that may not lock to the plate. The bone screws have to be long enough to bite into both sides of the vertebral body to gain enough strength to obtain the needed stability. These devices are difficult to place due to the length of the screws, and damage occurs when the screws are misplaced.

A third type of anterior fixation device comprises a hollow device that may or may not be externally threaded. The device is positioned between two adjacent vertebral bodies. Bone grafts from cadavers or from the pelvic region of the patient may be placed into the hollow center of the device. Bone morphogenic protein or other substances that promote bone growth can also be placed into the hollow center of the device. The cage might allow bone to grow through the device and fuse the two adjacent vertebrae.

Although the devices described above present various solutions, further improvement in this area is desirable. In particular, improved stabilization devices that enable a surgeon to reduce a vertebral displacement (e.g., of the type occurring in spondylolisthesis) prior to spinal fixation are needed.

SUMMARY

The present invention overcomes the drawbacks in the prior art by providing a reduction and stabilization device that allows a surgeon to reduce a misaligned vertebral body prior to spinal stabilization and/or fusion. For example, the present device may be used to treat a patient with spondylolisthesis by translating a misaligned vertebra over a distance ranging from zero to three centimeters or more. The present invention also overcomes drawbacks associated with the prior art by providing a reduction and stabilization device with improved intrinsic stability which can restore the proper height between adjacent vertebrae in one implant. Moreover, the reduction and stabilization device of the present invention may provide a greater area of space for bone grafts.

One aspect of the present invention provides a reduction and stabilization device for reducing and stabilizing two adjacent vertebral bodies in a spinal column. The reduction and stabilization device includes: a first plate adapted for fixation to the first of the two adjacent vertebral bodies; an intervertebral body having an extension adapted for positioning between the two adjacent vertebral bodies; a second plate attached to the intervertebral body and adapted for fixation to the second of the two adjacent vertebral bodies; and an adjustable connector adapted to connect the first and second plates. In a preferred embodiment, the second plate is adapted for fixation to both of the adjacent vertebral bodies at, for example, the side (anterior, posterior or lateral) of the bodies.

The first plate has a back face and an oppositely facing front face. The second plate also has a back face and an oppositely facing front face. The first and second plates can be connected by an adjustable connector that is adapted to adjust the anterior/posterior (or sagittal) distance between the first and second plates when the device is fixed to adjacent vertebral bodies in a spinal column. The adjustable connector may take a variety of forms, provided it allows for adjustment of the anterior/posterior (or sagittal) separation between the first and second plates. In one embodiment, the adjustable connector takes the form of at least one, and preferably two or more, threaded stem(s) extending outwardly from the front face of the first plate. The threaded stem(s) may be permanently or removably attached to the first plate. For example, the threaded stem(s) may be threaded such that they may be screwed into and out of threaded guide holes in the first plate. In this embodiment, the second plate defines at least one, and preferably two, reduction slot(s) through which the at least one threaded stem is adapted to pass when the reduction and stabilization device is fixed to the adjacent vertebral bodies. The reduction slot(s) can be of any shape, including circular, square, elliptical, etc. In this embodiment, the adjustable connector further includes a nut that screws over the at least one threaded stem and tightens against the front face of the second plate. In an exemplary embodiment, a portion of the threaded stem extending past the nut can be removed by any method known to those of skill in the art.

In another embodiment, the adjustable connector takes the form of a threaded shaft having a shaft head at its distal end adapted to screw into a threaded guide hole in the first plate. The threaded shaft can be inserted through the reduction slot of the second plate and into the guide hole of the first plate. The diameter of the shaft head can be larger than the diameter of the reduction slot such that the shaft head presses against the second plate as the threaded shaft is screwed into the guide hole of the first plate causing the second plate to translate toward the first plate as the screw is tightened. In one variation of this embodiment, the adjustable connector is part of a reduction tool having a handle attached to the shaft head. Optionally, the first plate can include one or more alignment pin(s). The alignment pin(s) can be detachably mounted to the first plate by threads, a snap-on mechanism, a Morris taper, or any other method known to those of skill in the art. Alternatively, the alignment pin(s) can be welded or otherwise permanently mounted to the first plate. The alignment pin(s) can pass through the reduction slot(s) of the second plate such that the second plate can be aligned relative to the first plate prior to the insertion of the adjustable connector. Once the second plate is properly aligned with the first plate, at least one of the alignment pins can be removed from the first plate. Finally, once the vertebral bodies are aligned, any additional alignment pin(s) can be removed, and plate fasteners can be inserted through the reduction slots and used to rigidly mount the second plate to the first plate and maintain the adjacent vertebral bodies in alignment. The plate fasteners can use threads, a snap-on mechanism, a Morris taper, or any mounting mechanism to mount the second plate to the first plate.

Adjustable connectors other than screw-type connectors may be used. For example, the adjustable connector may embody a ratchet mechanism or a pulley mechanism, instead of a screw-type mechanism.

The second plate may be composed of two or more sections. Typically, the intervertebral body is affixed to the back face of the second plate, and extends along a plane which is perpendicular to, or substantially perpendicular to, the back face of the second plate. In a preferred embodiment, the first and second plates are adapted for fixation to the anterior or lateral sides of the adjacent vertebral bodies. In a most preferred embodiment, the first and second plates are adapted for fixation to the anterior sides of the adjacent vertebral bodies.

The intervertebral body generally has an intervertebral extension with a first end (i.e., a leading end) and a second end (i.e., a trailing end) and opposing first and second surfaces for contacting the respective surfaces of the adjacent vertebral bodies. In some embodiments of the device, the intervertebral extension includes at least two legs attached to the back face of the second plate which are adapted for disposal between the adjacent vertebral bodies to provide support therebetween. In such embodiments, there is a space between two of the legs such that together with the second plate a U shape is formed as viewed superior to inferior. Preferably, the legs extend along the plane which is transverse to the plane of the second plate. More preferably, the legs extend along a plane which is substantially perpendicular to the plane of the second plate. However, the intervertebral body is not limited to this design. For example, in some embodiments of the device, the intervertebral body forms a ring, a disc, or a cylinder. In some embodiments, the intervertebral body may include a hollow cage. In some embodiments, the intervertebral body may be constructed and arranged to allow the stabilization device to flex superiorly and inferiorly when arranged between the vertebral bodies and prior to fusion of the vertebral bodies. In one embodiment, the stabilization device includes a slot extending transversely in a direction between anterior and posterior to allow the stabilization device to flex superiorly and inferiorly when arranged between the vertebral bodies and prior to fusion of the vertebral bodies. Further, the intervertebral body may be of different elasticity than the plates to allow the stabilization device to flex superiorly and inferiorly when arranged between the vertebral bodies and prior to fusion of the vertebral bodies. Suitable designs for the intervertebral body and the attached second plate are described in U.S. Pat. No. 6,461,359, the entire disclosure of which is incorporated herein by reference.

Another aspect of the present invention provides a method of reducing and stabilizing adjacent vertebral bodies. The method includes the steps of: fixing a first plate to the first of two adjacent vertebral bodies; inserting an intervertebral body between the two adjacent vertebral bodies, the intervertebral body attached to a second plate; fixing the second plate to the second of the two adjacent vertebral bodies, wherein the first and second plates are connected by an adjustable connector; and adjusting the adjustable connector to cause the first plate (and the misaligned vertebral body attached thereto) to translate toward the second plate, thereby bringing the first vertebral body into alignment with the second vertebral body. The first and second plates may be attached at various locations on the vertebral bodies, including the side (anterior, posterior or lateral).

In an exemplary embodiment, the method employs an adjustable connector that takes the form of at least one, and preferably two, threaded stem(s) extending outwardly from the front face of the first plate. In this embodiment, the second plate defines at least one, and preferably two or more reduction slot(s) (e.g., through hole(s)) through which the at least one threaded stem is adapted to pass when the stabilization device is fixed to the adjacent vertebral bodies. In this embodiment, the adjustable connector further includes a nut that screws over the at least one threaded stem. After the at least one threaded stem of the first plate is passed through the at least one through hole of the second plate, the adjustable connector is adjusted by tightening the nut on the at least one threaded stem against the front face of the second plate, causing the first plate (and the misaligned vertebral body attached thereto) to translate toward the second plate, thereby bringing the first vertebral body into alignment with the second vertebral body. Once the nut is fully tightened, the second plate may be fixed to the first of the two adjacent vertebral bodies and, if necessary or desirable, the portion of the at least one threaded stem that extends beyond the nut may be removed. If the threaded stem(s) are permanently fixed to the first plate, this may be accomplished, for example, by breaking the threaded stem at a pre-stressed location along its length. Fixing the first and second plates to their respective vertebral bodies may be accomplished by inserting at least one fixation member through an aperture in the plate and into the side of one of the adjacent vertebral bodies.

In another exemplary embodiment, the method employs an adjustable connector that takes the form of a threaded shaft having a shaft head at its distal end adapted to screw into a threaded guide hole in the first plate. The threaded shaft can be a portion of a screw, a portion of a reduction tool, or a portion of any other threaded mechanism which can be used to translate the first plate and the second plate toward one another. The threaded shaft is inserted through the reduction slot of the second plate and screwed into the guide hole of the first plate until the shaft head makes contact with the second plate. The surgeon may then continue to screw the threaded shaft into the guide hole, causing the second plate to translate toward the first plate as the screw is tightened, until the misaligned vertebral body is brought into alignment. Optionally, at this point the second plate may be rigidly fixed to the first of the two adjacent vertebral bodies and, if necessary or desirable, the adjustable connector may be removed. Fixing the first and second plates to their respective vertebral bodies may be accomplished by inserting at least one fixation member through an aperture in the plate and into one of the adjacent vertebral bodies. In an alternative embodiment, the method can employ an adjustable connector which takes the form of a clamp, a pulley, or a ratchet mechanism which can be used to translate the first plate and the second plate toward one another.

If the stabilization device includes an intervertebral body having at least two legs which define an approximate U-shape as viewed superior to inferior, the vertebral body may be inserted between the adjacent vertebral bodies such that the legs extend in a direction between anterior and posterior. In this embodiment, the method may also include the step of inserting a fixation member along the legs. In a more preferred embodiment, the legs may include a recess extending in a direction between anterior and posterior. The method may further include the step of inserting a leg fixation member within the recess such that the leg fixation member is partly in at least one of the adjacent vertebral bodies and partly in the recess along the axis of said leg. In an exemplary embodiment, the leg fixation member can also be received by an interference hole in the second plate.

In some embodiments, the stabilization device may also include a channel formed in at least one of the first and second surfaces of the intervertebral body. The channel may extend between the first and second ends of the intervertebral body. In a more preferred embodiment, the stabilization device may further include a fixation member having a width which, when positioned for fixation, is partially in one of the vertebral bodies, the remaining portion being exterior to the vertebral bodies, preferably within the intervertebral body.

In another aspect of the invention, a kit is provided that includes at least one first plate adapted for fixation to the anterior, lateral or posterior sides of one of two adjacent vertebral bodies. The at least one first plate has a back face and an oppositely facing front face. The kit further includes at least one second plate adapted for fixation to the anterior, lateral or posterior sides of one, or both, of two adjacent vertebral bodies. The at least one second plate has a back face and an oppositely facing front face. At least one adjustable connector adapted to connect the at least one first plate and the at least one second plate is also included in the kit. Alternatively, one or more alignment pins can be included in the kit.

The at least one adjustable connector may be adapted to be permanently or removably connected to the first and second plates. The kit also includes at least one intervertebral body adapted for attachment to the back face of the at least one second plate, such that it extends along a plane which is perpendicular to, or substantially perpendicular to, the back face of the second plate. The at least one intervertebral body has a first end (i.e., a leading end) and a second end (i.e., a trailing end) and opposing first and second surfaces adapted for contacting the respective surfaces of the adjacent vertebral bodies. Each kit includes a plurality of one or more of the four components (i.e., the first plate, the second plate, the adjustable connector and the intervertebral body) having different sizes and/or shapes, such that components having different sizes and shapes may be selected to fit a particular patient.

BRIEF DESCRIPTION OF THE DRAWINGS

FIG. 4 is a front view of a locking plate mounted to the second plate of the reduction and stabilization device in accordance with an exemplary embodiment.

FIG. 5 is a kit having two intervertebral bodies and two second plates in accordance with an exemplary embodiment.

DETAILED DESCRIPTION

Figure 1B:
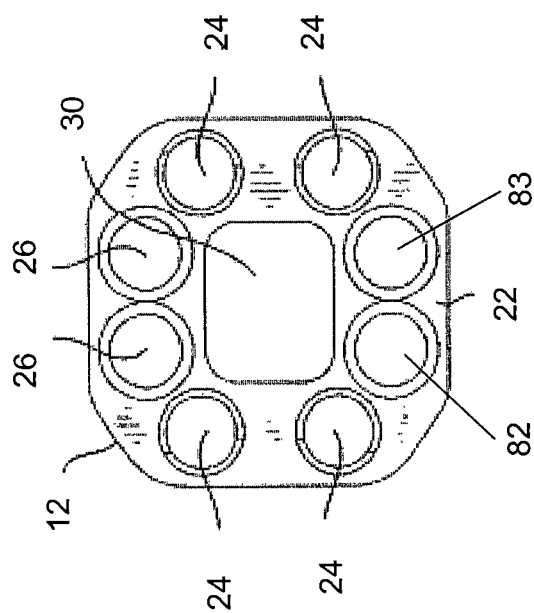
FIG. 1B is a front elevation view of the intervertebral body and second plate of FIG. 1A.
Figure 1A:
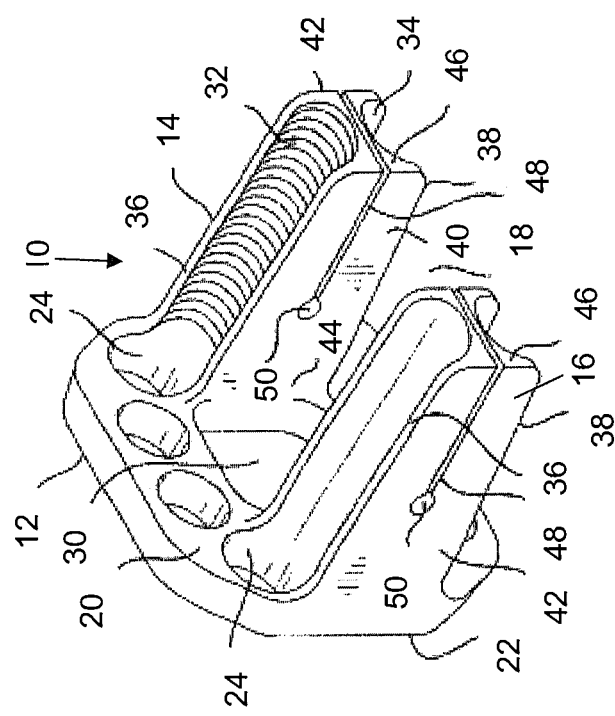
FIG. 1A is a rear perspective view of one embodiment of a intervertebral body and second plate of a stabilization device in accordance with the present invention.

Referring to FIGS. 1A, 1B, 2A and 2B, the basic components of a stabilization device in accordance with one illustrative embodiment of the present invention are generally designated as 10. The device, which is constructed of biocompatible material, includes a first plate 11. The device 10 further includes a second plate 12. The intervertebral body of device 10 includes legs 14 and 16 attached to the back face 20 of second plate 12. As shown in FIG. 1A, the legs may extend along a plane which is substantially perpendicular to the plane of the back face 20 of the second plate 12, there being a space 18 between the legs such that together with the back face 20 of the second plate 12 the legs form a U shape as viewed superior to inferior. However, it should be understood that the legs may extend in other planes with respect to the plane of the second plate while still maintaining a generally U-shaped configuration. Of course, in other embodiments, a U shape may not be formed as other arrangements of the legs and second plate are established. For example, one leg or three legs might be provided. In still other embodiments, the intervertebral body may include an intervertebral extension that is not in the form of legs. For example, the intervertebral extension may be a ring.

Figure 2B:
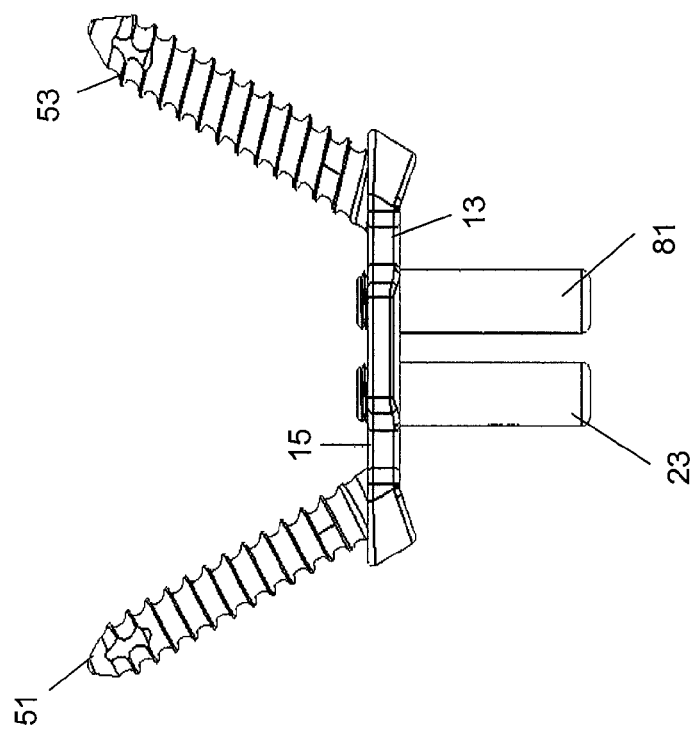
FIG. 2B is a superior elevation view of the first plate including alignment pins.

First plate 11 has a front face 13, which faces away from a vertebral body, and a back face 15, which faces toward the vertebral body, and includes through holes 17 and 19 extending from front face 13 to the back face 15, through which fixation members, such as bone screws, may be inserted. Through holes 17 and 19 are substantially symmetrically opposed between the right and left halves of first plate 11. In FIGS. 2B and 4, it can be seen that fixation members 51 and 53 are inserted into through holes 17 and 19 to fix first plate 11 to a first vertebral body, as will be discussed in detail below. The fixation members are desirably bone screws having a length in the range of approximately 20-80 millimeters, such that bicorticle purchase in the vertebral body (or sacrum) can be achieved. Alternatively, the surgeon can use any type and/or length of fastener which is capable of mounting the first plate to a vertebral body. Mounting of the first plate 11 to the vertebral body is described in more detail with reference to FIGS. 6 and 7A-7D.

Figure 2A:
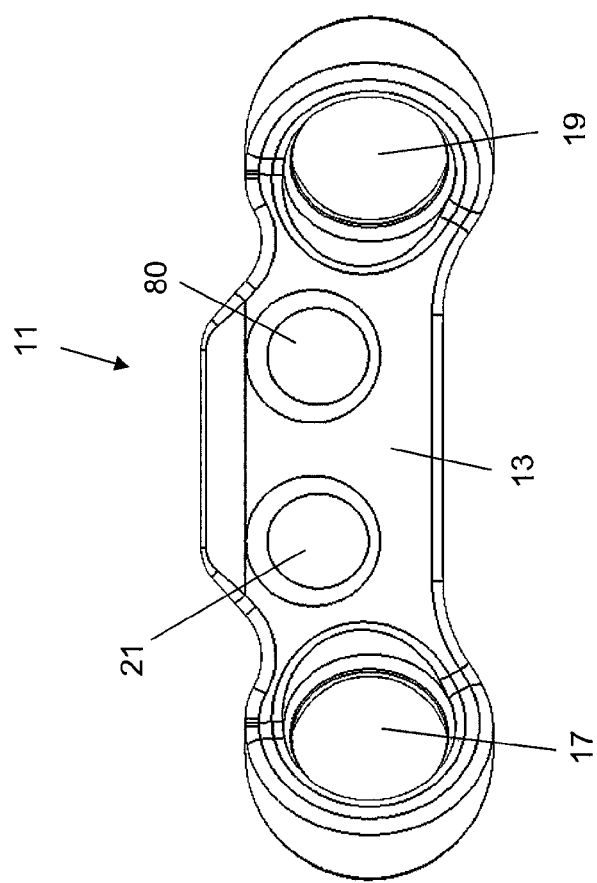
FIG. 2A is a front elevation view of a first plate of a reduction and stabilization device.

The exemplary embodiments illustrated in FIGS. 2A and 2B show the first plate 11 as an elongated structure with rounded ends. In alternative embodiments, the first plate can take on any other shape including circular, square, crescent, hexagonal, elliptical, octagonal, etc. such that the first plate is capable of being mounted to a vertebral body. In an exemplary embodiment, the first plate 11 is shaped to facilitate fixation to an anterior portion of a vertebral body. Alternatively, the first plate can be shaped to facilitate fixation to a lateral or posterior portion of the vertebral body. In another exemplary embodiment, the first plate 11 is shaped to facilitate fixation to the first sacral vertebra (the S-1 vertebra). Alternatively, the first plate can be shaped to facilitate fixation to any vertebral body.

Optionally, the first plate 11 also includes two guide holes 21 and 80 which can extend from the front face 13 to the back face 15. In an exemplary embodiment, the guide holes 21 and 80 can be capable of receiving alignment pins 23 and 81 such that the second plate 12 can be lined up properly with and/or secured to the first plate 11. The alignment can be implemented by ensuring that the alignment pins 23 and 81 pass through reduction slots of the second plate 12, as described below. Once the second plate 12 is properly aligned, at least one of the alignment pins 23 and 81 can be removed. In an exemplary embodiment, the guide holes 21 and 80 can be threaded such that the alignment pins 23 and 81 can be screwed into and removed from the first plate 11.

Second plate 12 has a back face 20 which faces toward a vertebral body, and a front face 22 which faces away from the vertebral body. As illustrated with reference to FIG. 1B, the second plate 12 is octagonal in shape. However, in alternative embodiments, the second plate can be any shape, including circular, crescent, square, hexagonal, etc., as long as the second plate is capable of being fixed to a vertebral body. In an exemplary embodiment, the second plate 12 is shaped to facilitate fixation to the fifth lumbar vertebra (the L-5 vertebra). Alternatively, the second plate can be shaped to facilitate fixation to any vertebral body.

The second plate 12 may include interference holes 24, the reduction slots 82 and 83, and through holes 26. The interference holes 24, the reduction slots 82 and 83, and/or the through holes 26 can be threaded or unthreaded depending on the embodiment. As illustrated with reference to FIGS. 1A and 1B, the interference holes 24, the reduction slots 82 and 83, and the through holes 26 extend from the front face 22 of the second plate 12 to the back face 20 of the second plate 12. In addition, the interference holes 24 terminate in line with the channels 32 and 34 of the legs 14 and 16. In an exemplary embodiment, the interference holes 24 are substantially symmetrically opposed between top and bottom halves of the second plate 12. The interference holes 24 can be capable of receiving fixation members such that the second plate 12 can be more securely mounted to a first vertebral body to which the first plate 11 is mounted and/or a second vertebral body to which the second plate 12 is mounted. The through holes 26 are capable of receiving fixation members such that the second plate 12 can be mounted to the second vertebral body upon which the first plate 11 is mounted.

The reduction slots 82 and 83 of the second plate 12 can serve a number of purposes. The reduction slots 82 and 83 can receive the alignment pins 23 and 81 described with reference to FIG. 2B such that the second plate 12 can be properly aligned relative to the first plate 11 and the second vertebral body. Alternatively, the reduction slots 82 and 83 can receive threaded stems which extend outwardly from the first plate 11, as described in greater detail with respect to FIGS. 15A-15C, below. The reduction slots 82 and 83 can also receive a threaded end of a reduction tool, as described in more detail with reference to FIGS. 12 and 13. The reduction slots 82 and 83 can also receive plate fasteners such that the second plate 12 can be mounted to the first plate 11. In an exemplary embodiment, the reduction slots 82 and 83 can be vertically oblong to provide a small amount of play for aligning the second plate 12 relative to the first plate 11. Alternatively, the reduction slots can be horizontally oblong, or any other shape capable of receiving alignment pins, threaded stems, plate fasteners, and/or any type of reduction tool.

The fixation members used to fix the first and second plates to vertebral bodies may be any type of suitable fastener, such as an anchor, screw, dowel, etc. Preferably, the fixation members are screws. More preferably, the screws have a threaded head which mates with threads in the through holes so as to threadedly connect the screws to the first and second plates. Alternatively, the fixation members may be polyaxial screws which permit the screws to be inserted at a variety of angles. Additionally, some or all of the through holes may be replaced with a slot to allow a surgeon greater control over the positioning of a fixation member. The present invention is not limited to any particular configuration of the through holes in the first and second plates.

In a preferred embodiment, second plate 12 may further include an aperture 30, which provides access to space 18. Aperture 30 can be any shape which allows access to space 18, including circular, hexagonal, crescent, square, rectangular, octagonal, elliptical, triangular, etc. Bone fragments, bone growth factors, other materials promoting the growth of bone, blood vessels or other tissue, or materials used in a reduction procedure may be packed into device 10 through aperture 30. In an alternative embodiment, second plate 12 may not include aperture 30 or may include smaller apertures in place of a single aperture. In embodiments having no apertures at all, the device might be packed with any of the above materials prior to placement of device 10 between adjacent vertebrae.

Figure 10:
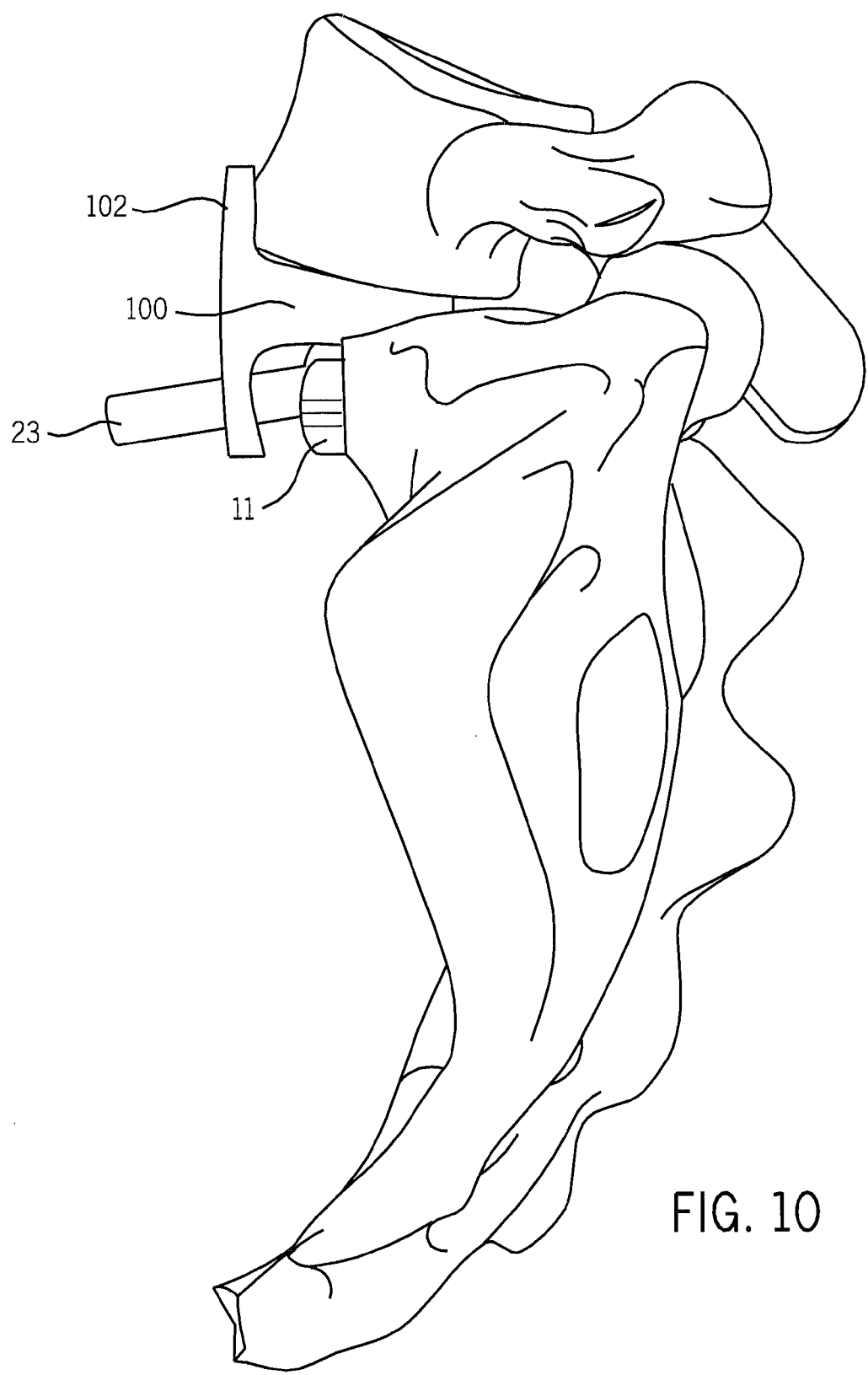
FIG. 10 is a side view of a mounted first plate acting as a guide for mounting the second plate in accordance with an exemplary embodiment.

The intervertebral body 10 of the reduction and stabilization device may be mounted to the back face 20 of the second plate 12. As used in this disclosure, the term "mount" can include join, unite, connect, associate, insert, hang, hold, affix, attach, fasten, bind, paste, secure, bolt, nail, glue, screw, rivet, solder, weld, and other like terms. The intervertebral body 10 can be permanently or removably mounted to the second plate 12, depending on the embodiment. In the illustrative embodiment of FIGS. 1A, 1B, 2A and 2B, the intervertebral body includes legs 14 and 16. In some embodiments, the two legs may not be substantially the same, but in the preferred embodiment they are. Therefore, the following description of leg 14 may also apply to leg 16. Leg 14 includes a first surface 36 and a second surface 38 for contacting the respective surfaces of adjacent vertebral bodies. The leg has sufficient strength and rigidity to maintain the vertebrae in a desired spatial relationship, as shown in FIG. 10. This may include a shaping and/or sizing of the leg. The leg may taper from larger to smaller from anterior to posterior, to more anatomically imitate the space that should be maintained between the vertebral bodies. However, it should be understood that other shapes may be used to maintain the desired spatial relationship between the vertebral bodies and still be within the scope of the invention. The legs also have opposing inner surfaces 40 as well as outer surfaces 42 spaced apart laterally and extending longitudinally from a proximal end 44 to a distal end 46.

The legs may further include channels 32 and 34 which are substantially symmetrically opposed on the superior and inferior sides of leg 14. Preferably, the channels 32 and 34 are cylindrical in shape. The channels 32 and 34 may be threaded and permit the insertion of a fixation member into a vertebral body. The channels may extend for substantially the entire length of the legs as shown in FIG. 1A. However, it is contemplated that the channels need not extend the entire length of the leg, thus permitting a surgeon to insert the fixation member along axes not substantially parallel to the axis of the leg.

Preferably, a fixation member inserted into channel 34 is sized so that when positioned for fixation, a portion of the fixation member extends beyond surface 38 of leg 14 and engages the bone of a first vertebral body. Similarly, a fixation member inserted into channel 32 is sized so that when positioned for fixation, a portion of the fixation member extends beyond surface 36 of leg 14 and engages the bone of a second vertebral body. Each fixation member inserted through a channel engages only one of the vertebral bodies. In one embodiment, at least about 25% of the width of the fixation member is in one of the vertebral bodies. In another embodiment, about 25% to about 50% of the width of the fixation member is in one of the vertebral bodies. In yet another embodiment, about 50% to about 100% of the width of the fixation member is in one of the vertebral bodies. The fixation members are preferably comprised of titanium but may also be comprised of stainless steel, ceramics, composite materials, other materials known in the surgical and medical arts, and/or biologically inert materials may be used.

The legs may also include a flexing feature, which by structure or material permits device 10 to flex superiorly and inferiorly when arranged between the vertebral bodies and prior to fusion of the vertebral bodies. Preferably, this feature is facilitated by slot 48, which extends substantially parallel to the plane of the leg. More preferably, slot 48 extends from distal end 46 to a relief opening 50. Most preferably, slot 48 is also provided to extend from the inner surface 40 to outer surface 42. In an alternative embodiment, slot 48 extends longitudinally from the front face 22 of the second plate to a relief opening 50 in leg 14. It is contemplated, however, that a slot extending from distal end 46 to relief opening 50 may provide greater flexibility to device 10. Other embodiments are also contemplated which would permit the device to flex. For example, a hinge of any suitable type might be constructed or materials of different elasticity might be used in the plates and intervertebral body. The first plate 11, the second plate 12, and/or the intervertebral body may be constructed of a metal such as titanium or stainless steel, a more pliable material such as polyethylene or polyether ether ketone ("PEEK"), polyurethane, carbon, hydroxyapetite, bone, or ultra high molecular weight polyethylene ("UHMWPE").

In an alternative embodiment, legs 14 and 16 may also include a bridging member 52 to provide additional stability or support to device 10. The location of bridging member 52 in relation to legs 14 and 16 may be varied in alternative embodiments of the invention. Bridging member 52 can be at any position along the legs 14 and 16, but in one preferred embodiment the bridging member is positioned at the ends 46 of the legs 14 and 16. The bridging member or members may have the same height as the legs at its point of connection or may vary in height.

Figure 1C:
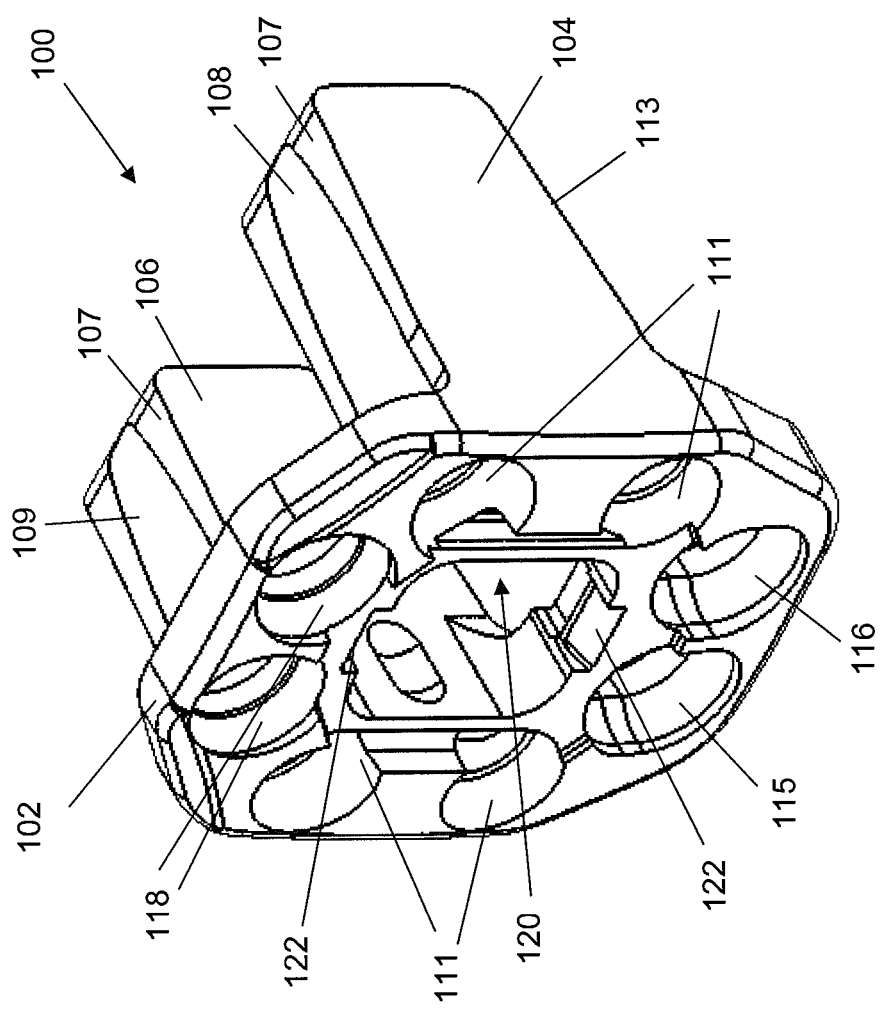
FIG. 1C is a front perspective view of an intervertebral body mounted to a second plate in accordance with a second exemplary embodiment.
Figure 3B:
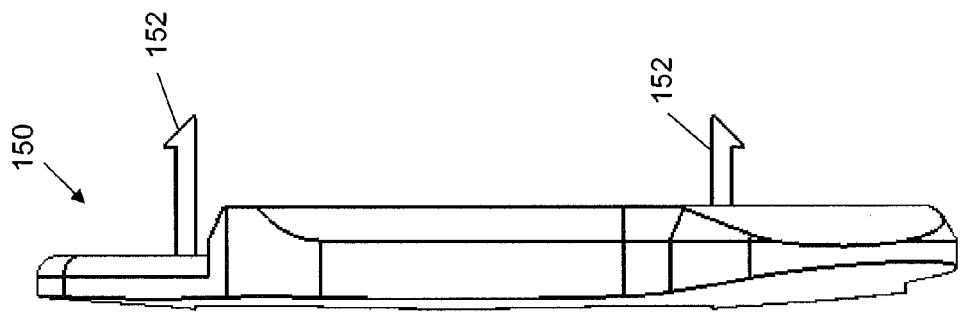
FIG. 3B is a side view of the locking plate in accordance with an exemplary embodiment.
Figure 3A:
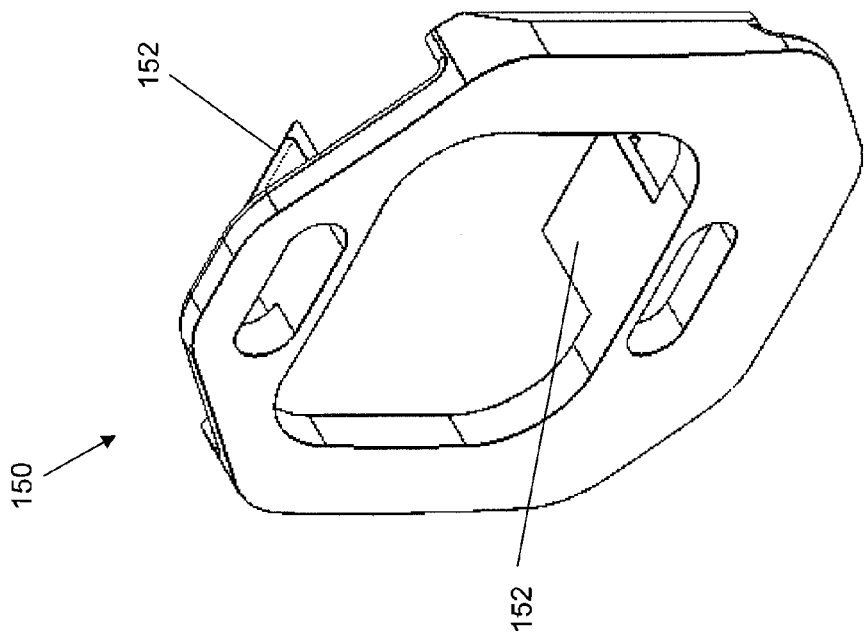
FIG. 3A is a front perspective view of a locking plate in accordance with an exemplary embodiment.

FIG. 1C illustrates an intervertebral body 100 mounted to a second plate 102. This embodiment is similar to the embodiment depicted in FIGS. 1A and 1B with various modifications. The intervertebral body 100 includes legs 104 and 106 with channels 108 and 109 in a superior surface 107 of the legs 104 and 106. In an exemplary embodiment, the legs 104 and 106 can also include channels (not shown) in an inferior surface 113 of the legs 104 and 106. The second plate 102 includes interference holes 111, reduction slots 115 and 116, and through holes 118. The second plate 102 also includes an opening 120 with two receiving slots 122 such that a locking plate 150, as illustrated with reference to FIGS. 3A and 3B, can be mounted to the second plate 102. The receiving slots 122 can be tapered surfaces capable of receiving one or more mounting protrusions 152 of the locking plate 150. Alternatively, there can be any number of receiving slots, and the receiving slots can be of any shape and/or configuration such that the locking plate 150 can be securely mounted to the second plate 102. Similarly, in alternative embodiments, the locking plate can include any number, shape, and/or configuration of mounting protrusions.

FIG. 4 is a front view illustrating the locking plate 150 mounted to the second plate 102 in accordance with an exemplary embodiment. In an exemplary embodiment, when the locking plate 150 is mounted on the second plate 102, at least a portion of the locking plate 150 covers at least a portion of the interference holes 111, the reduction slots 115 and 116, and the through holes 118. As such, the locking plate 150 can be used to ensure that any fixation members 127 received by the interference holes 111, plate fasteners 129 received by the reduction slots 115 and 116, and fixation members 127 received by the through holes 118 are not able to back out or come loose on their own once the surgery is complete. The locking plate 150 can also be used to help ensure that any grafting or other materials used for spinal fusion remain in place. In another exemplary embodiment, the second plate 102 can be mounted such that at least a portion of the second plate 102 covers at least a portion of the through holes 17 and 19 of the first plate 11. As such, the fixation members 51 and 53 used to mount the first plate 11 to the first vertebral body are not able to back out or come loose on their own.

The stabilization device may be a modular unit 110 (FIG. 5) in the form of a kit which permits the use of separate and different sized first and second plates and/or intervertebral bodies to accommodate for the varying sizes of vertebral bodies. As best seen in FIG. 5, a first plate and an adjustable connector, a second plate 112 and an intervertebral body 114 may be separate components which are attached in any suitable manner, e.g., through the use of screws, anchors, expansion arms, dowels, etc., as well as means developed in the future. Thus, a surgeon who is performing an anterior fixation surgery can isolate the spine using well-known surgical techniques and place appropriate sized and shaped first and second plates and intervertebral bodies from the kit into the intervertebral space of two adjacent vertebrae. The kit includes a plurality of one or more of the four components (i.e., the first plate, the second plate, the adjustable connector and the intervertebral body), having different sizes and/or shapes, such that components having different sizes and shapes may be selected to fit a particular patient. If the intervertebral body or plates are too large or too small, the plates or intervertebral body can be removed and replaced with plates or an intervertebral body of a more appropriate size and/or shape.

As discussed above, stabilization device 10 may be placed either anteriorly, laterally, or posteriorly between adjacent vertebrae of a spine and seated upon confronting end plates of the adjacent vertebral bodies to maintain a desired orientation and spacing between the adjacent vertebral bodies. The device may also support the adjacent vertebral bodies for fusion at the desired orientation and spacing in the treatment of patients with spondylolisthesis, ruptured or otherwise degenerative intervertebral discs, vertebral trauma, tumors, etc. In a preferred embodiment, stabilization device 10 is inserted anteriorly or laterally. More preferably, stabilization device 10 is inserted anteriorly. Anterior insertion provides several benefits over posterior insertion. For example, in anterior spinal surgery the surgeon is able to selectively place the first plate 11 on a first vertebral body such that the first plate 11 avoids the vasculature on the anterior side of the first vertebral body. The surgeon can also achieve bicorticle purchase with the fixation members (i.e., the fixation members can go into the anterior side of the first vertebral body and out through the posterior or lateral side of the first vertebral body) used to mount the first plate 11 to the first vertebral body (or sacrum). In a posterior spinal surgery, bicorticle purchase cannot be achieved without the risk of puncturing the vasculature on the anterior side of the vertebral body.

The discussion that follows describes methods for using the present spinal reduction and stabilization devices to correct a misalignment of the spine. Much of the description which follows assumes a misalignment of the fifth lumbar vertebra (L-5 vertebra) relative to the first sacral vertebra (S-1 vertebra). However, this description is not meant to be limiting, as the devices and methods described herein can be used relative to any misaligned vertebral body.

A patient undergoing anterior spinal surgery can be prepped by a surgeon prior to surgery as known to those skilled in the art. Once the patient is prepped, the surgeon can use X-ray assistance to plan an incision such that the problematic vertebra(e) can be accessed. In a surgery to correct the L-5 vertebra, the surgeon can make the incision parallel to or below the endplate of the S-1 vertebra. Once the incision is made, the surgeon can use a retroperitoneal approach to achieve access to the problematic vertebra(e). The surgeon can also mobilize and protect local vasculature on or near the anterior side of the vertebral bodies upon which surgery is being performed. The surgeon can also remove posterior osteophytes and/or the intervertebral disc by any method known to those of skill in the art. In an exemplary embodiment, the surgeon can also prepare the endplates of the adjacent vertebral bodies such that surgical tools and/or an intervertebral body can be effectively received on a smooth, flat surface. Endplate preparation can be performed by any method known to those of skill in the art.

Figure 6:
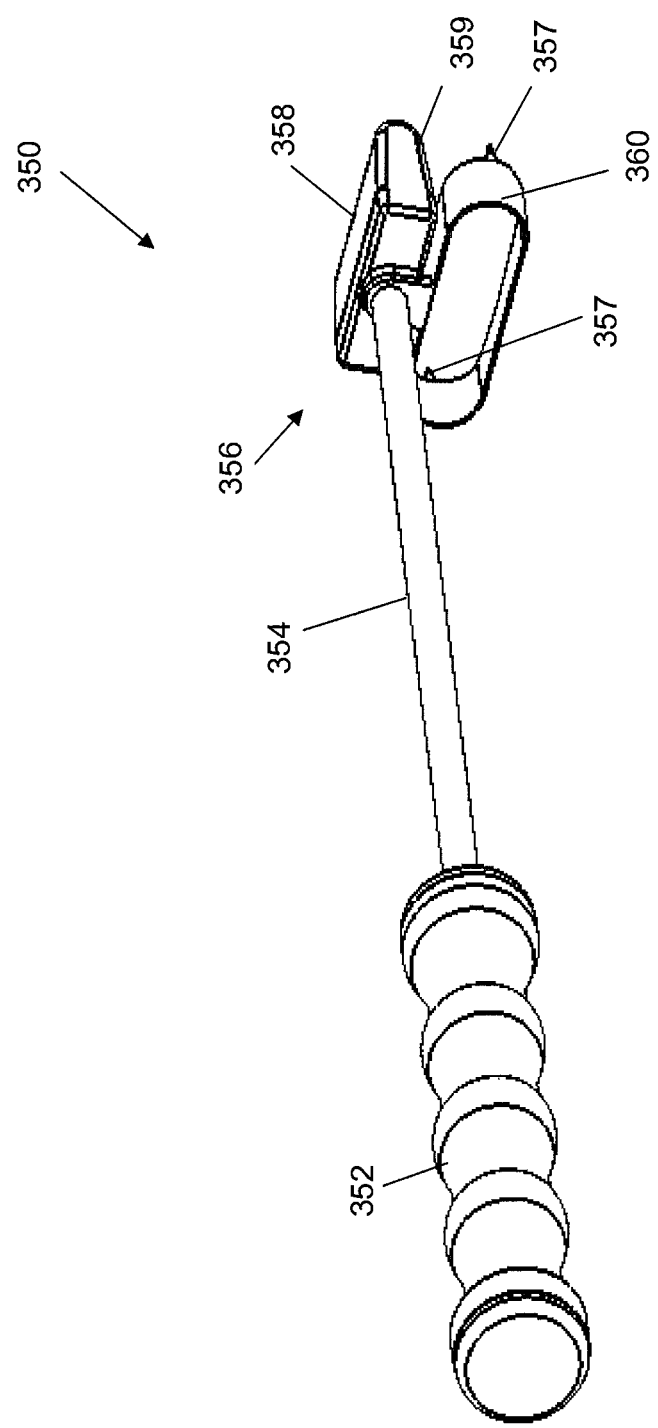
FIG. 6 is a rear perspective view of a mill guide tool in accordance with an exemplary embodiment.

Once the vertebral bodies have been isolated and/or prepared, the surgeon can attempt to passively distract any misalignment between the vertebral bodies. Methods and tools for the passive distraction of vertebral bodies are known and commercially available. In the event the passive distraction does not result in the realignment of the vertebrae, the surgeon can prepare the patient to receive the first plate 11 of the reduction and stabilization device. In an exemplary embodiment, preparation can include isolating an anterior portion of a vertebral body to which the first plate 11 is to be mounted. Preparation can also include ensuring that the first plate 11 is able to lie flush on the isolated anterior portion of the vertebral body by shaping the vertebral body with a burr tool or other shaping instrument. FIG. 6 illustrates a mill guide tool 350 which the surgeon can use to help shape a surface of a vertebral body and mount the first plate 11.

The mill guide tool 350 includes a handle 352, a shaft 354, and an alignment mechanism 356. In an exemplary embodiment, the handle 352 and the shaft 354 of the mill guide tool 356 can be mounted easily to and detached from the alignment mechanism 356. For example, an end of the shaft 354 can be threaded and the alignment mechanism 356 can include a threaded aperture for receiving the threaded end of the shaft 354. The alignment mechanism 356 includes a wedge 358 capable of maintaining a spacing between and/or orientation of adjacent vertebral bodies. In an exemplary embodiment, the wedge 358 can be the same size and/or shape as the intervertebral body which the surgeon plans to insert between the vertebral bodies. Alternatively, the wedge can be any size or shape which allows the wedge to fit between and/or maintain adjacent vertebral bodies.

Figure 7A:
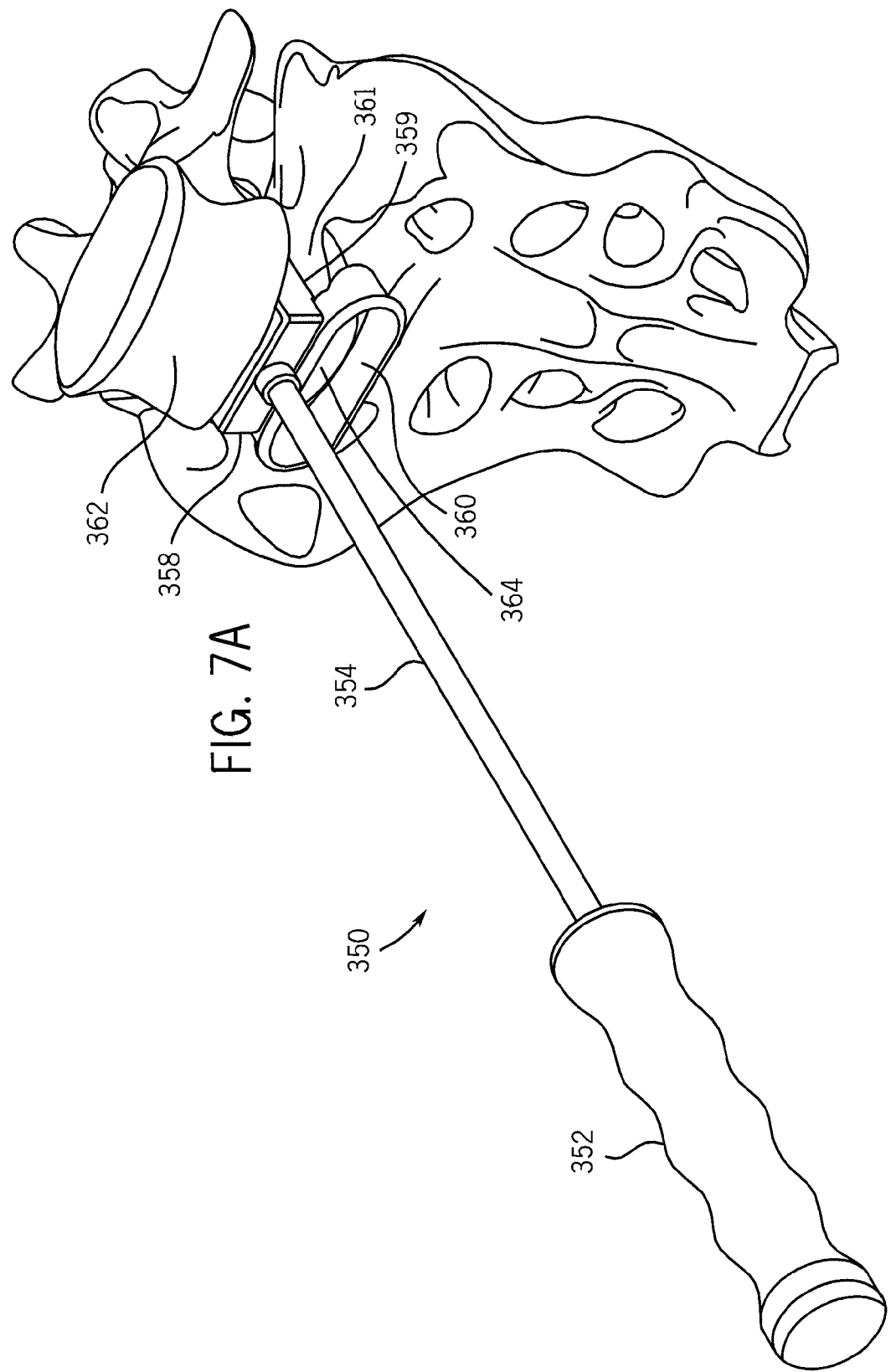
FIGS. 7A-7D illustrate operations performed during a mounting of the first plate in accordance with an exemplary embodiment.

The alignment mechanism 356 also includes a mill guide 360 capable of receiving a cutting end of a milling or shaping tool. The mill guide 360 is also capable of receiving the first plate 11 such that the first plate 11 can be mounted. As shown here, the mill guide 360 defines an oblong aperture having a circumferential shape that matches, or is substantially similar to, the circumferential shape of the first plate 11. The mill guide 360 may include one or more guide stabilizers 357. The one or more guide stabilizers 357 can be pressed into the first vertebral body to ensure that the alignment mechanism 356 does not move while the first plate 11 is being mounted. In an exemplary embodiment, the wedge 358 can be inserted between adjacent vertebral bodies such that a bottom surface 359 of the wedge 358 rests flat on an endplate of the lower vertebral body. The mill guide 360 can be coupled to the wedge 358 such that when the bottom surface 359 of the wedge 358 is resting on the endplate, the mill guide 360 is in an optimal location for placement of the first plate 11. In an exemplary embodiment, the mill guide 360 can be substantially the same size and shape as the first plate 11 to be used on the patient. FIG. 7A is a perspective view illustrating the mill guide tool 350 inserted between an S-1 vertebra 364 and an L-5 vertebra 362 in accordance with an exemplary embodiment. The wedge 358 has been inserted such that the bottom surface 359 of the wedge 358 is resting flat on an endplate 361 of the S-1 vertebra 364. As such, the mill guide 360 is optimally positioned to receive the first plate 11.

In an exemplary embodiment, the surgeon can use the mill guide tool to shape the surface of the vertebral body which will receive the first plate 11 prior to mounting the first plate 11 thereto. Shaping can be done while the mill guide tool 350 is still in place between adjacent vertebral bodies. As such, the mill guide 360 can be used as a guide to define an area of the vertebral body for the surgeon to shape. In an exemplary embodiment, the surgeon can use an end-cutting burr to shape the surface of the vertebral body. Alternatively, the surgeon can use any shaping instrument known to those of skill in the art. The vertebral body can be shaped to form a flat mounting surface on the vertebral body which is substantially perpendicular to a plane containing the endplate of the vertebral body. To improve access to the mill guide 360, the surgeon can remove the handle 352 and the shaft 354 from the mill guide tool 350 prior to using the shaping instrument and/or prior to inserting the first plate.

Figure 7B:
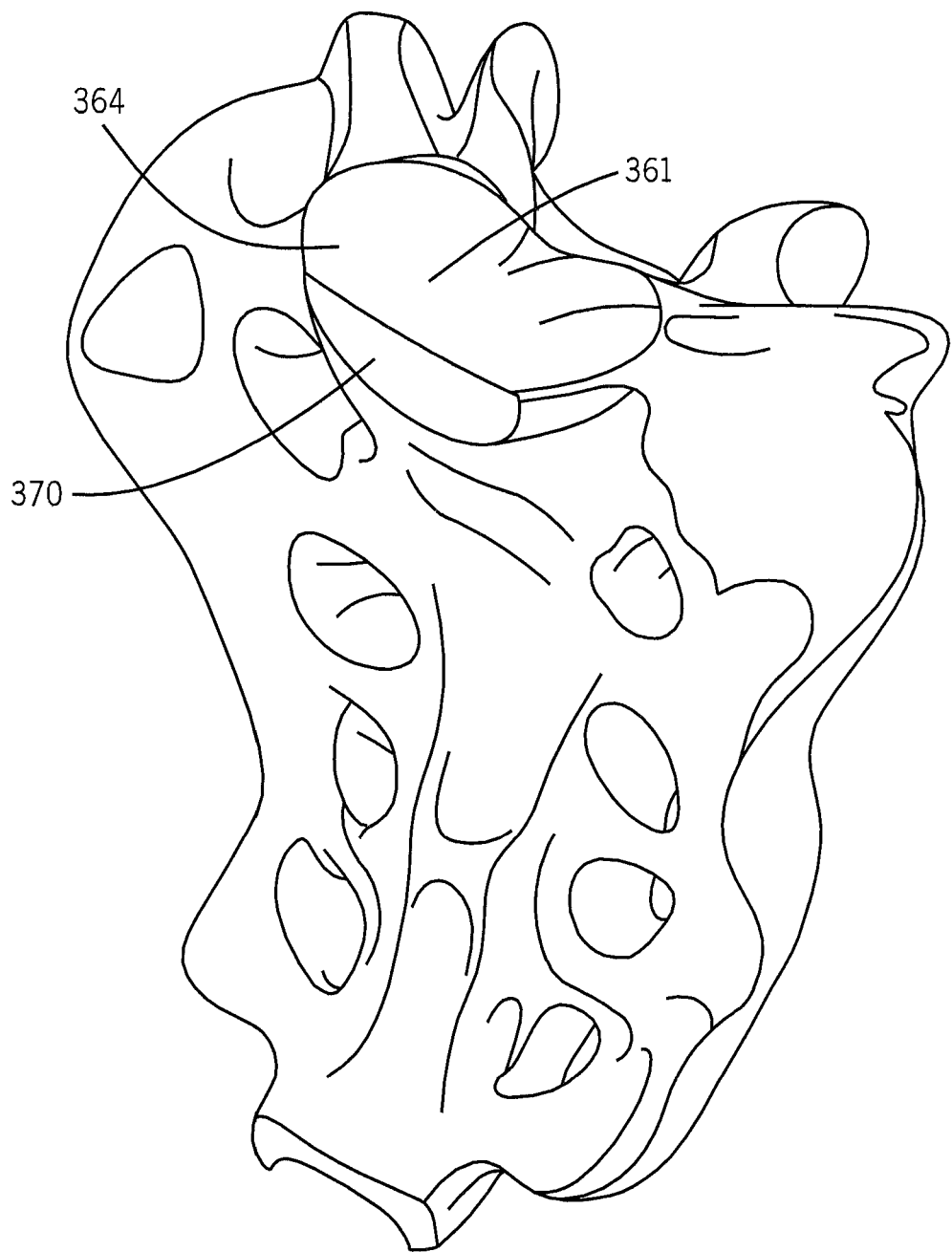

FIG. 7B is a perspective view illustrating the S-1 vertebra 364 after the surgeon has used a shaping instrument in accordance with an exemplary embodiment. As illustrated, the surgeon has shaped a mounting surface 370 for receiving the first plate 11. Further, the mounting surface 370 is substantially perpendicular to a plane containing the endplate 361 of the S-1 vertebra 364. FIG. 7B illustrates the alignment mechanism 356 of the mill guide tool 350 removed prior to mounting the first plate 11. This is for illustrative purposes, and is not meant to be limiting. In an exemplary embodiment, the alignment mechanism 356 of the mill guide tool 350 is not removed until after the first plate 11 is mounted to the vertebral body. Alternatively, the alignment mechanism 356 can be temporarily removed for cleaning bone fragments, etc., and then reinserted such that the first plate 11 can be mounted.

Figure 7C:
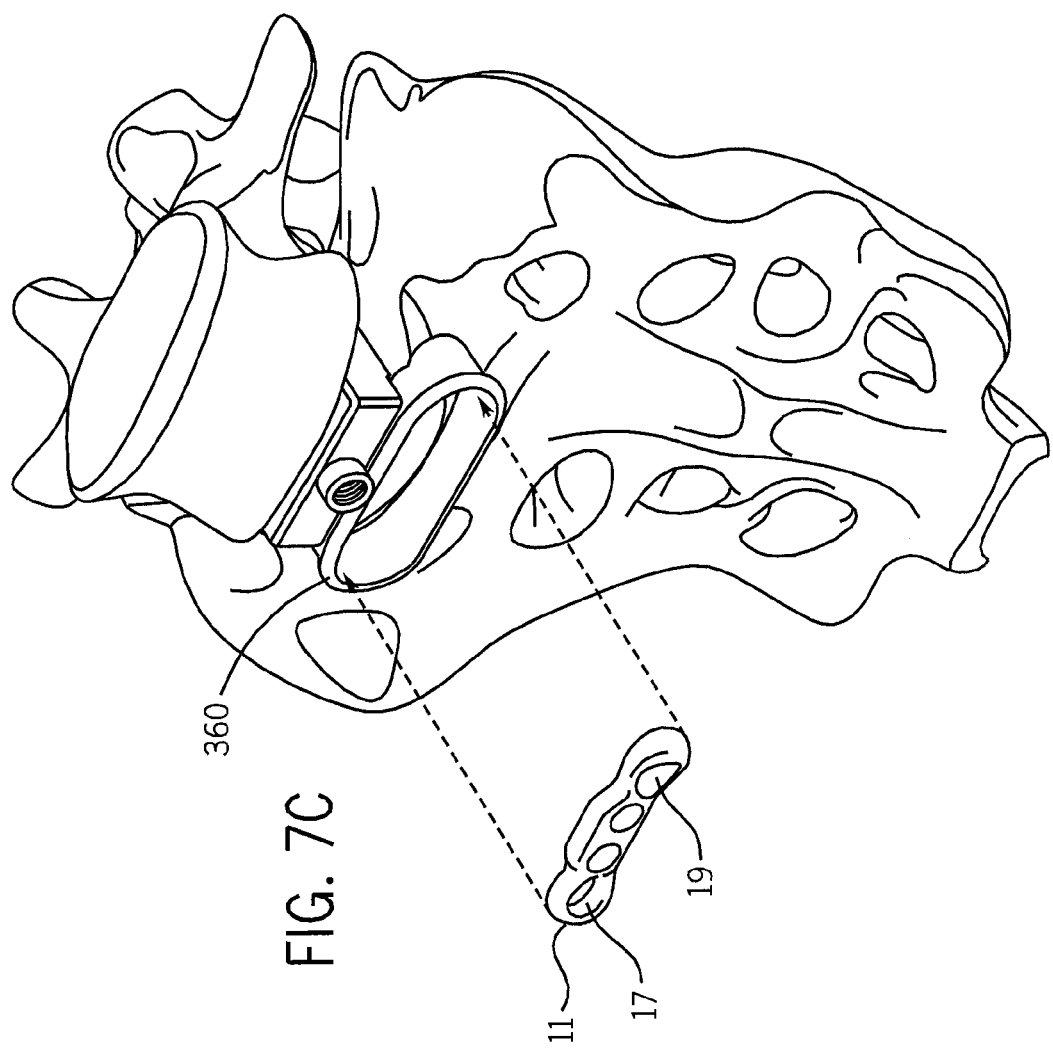

Once the vertebral body is prepared to receive the first plate 11, the surgeon can insert the first plate 11 through the mill guide 360 as illustrated with reference to FIG. 7C. Once the first plate 11 is inserted, it can be mounted to the vertebral body with the fixation members 51 and 53 described with reference to FIG. 2B, or other fixation members depending on the embodiment. The fixation members used to mount the first plate can be any type of suitable fastener, such as an anchor, screw, dowel, etc. In an exemplary embodiment, the fixation members are screws. The screws can be received by the through holes 17 and 19 of the first plate 11. In another exemplary embodiment, the through holes 17 and 19 can be threaded such that threads on the screws can mate with threads of the through holes 17 and 19. Alternatively, the through holes of the first plate 11 can be unthreaded and capable of receiving the fixation members. In another alternative embodiment, the fixation members can be polyaxial screws which are capable of being inserted through the first plate 11 at a variety of angles relative to the vertebral body.

Figure 7D:
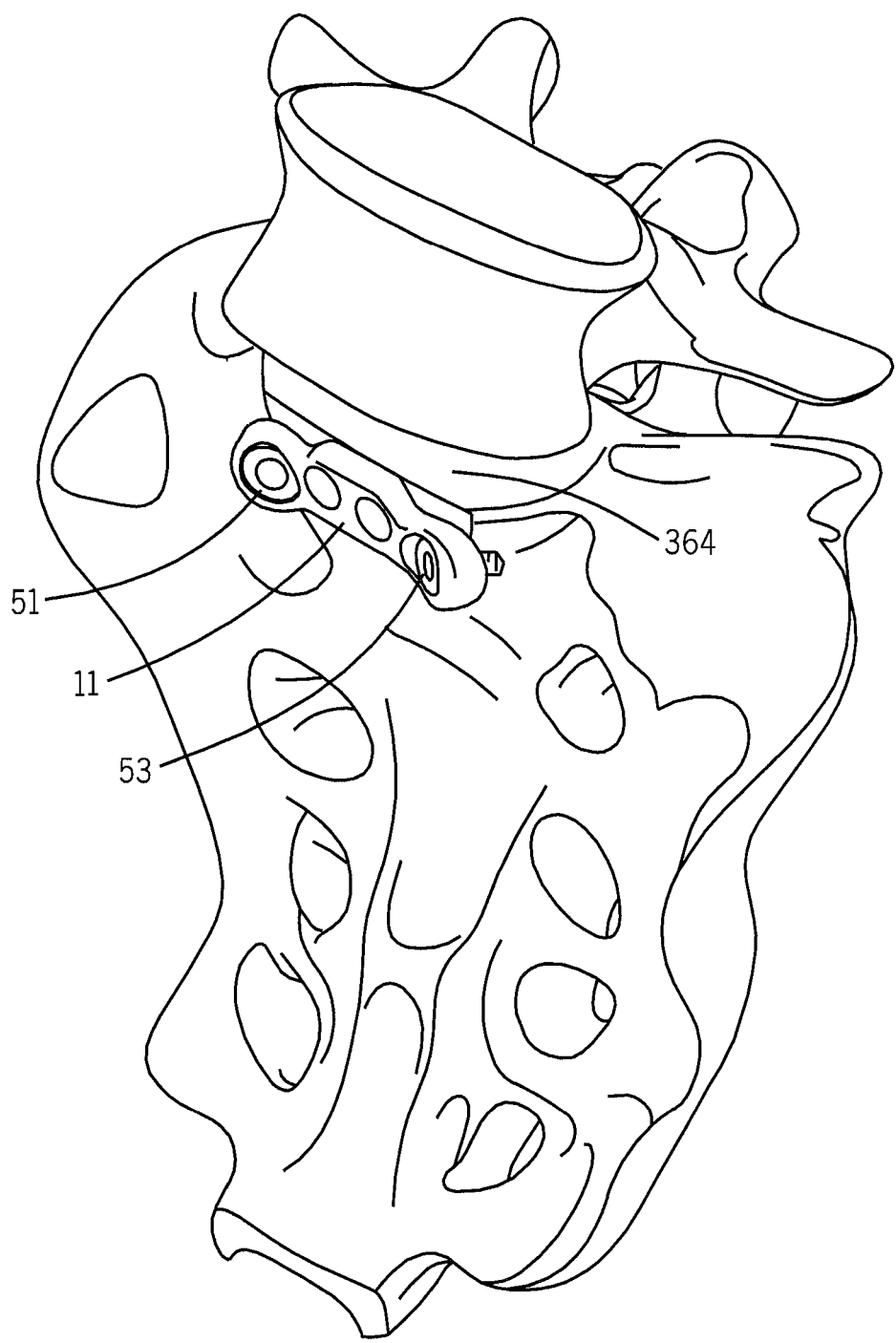

The surgeon can insert the fixation members into the vertebral body by any method known to those of skill in the art. For example, the surgeon can use a handheld screwdriver, a drill, a mallet, or any other tool capable of inserting the fixation members. The surgeon can also tap or drill pilot holes into the vertebral body prior to inserting the fixation members to help prevent bone fracture. In an exemplary embodiment, the fixation members can be placed with the assistance of fluoroscopy and may be either unicortical or bicortical in purchase. In a preferred arrangement, the fixation members are placed bicortically into the sacral ala to maximize purchase. FIG. 7D is a perspective view illustrating the first plate 11 mounted to the S-1 vertebra 364 in accordance with an exemplary embodiment. As illustrated, fixation members 51 and 53 have been inserted into the sacrum. In an exemplary embodiment, the alignment mechanism 356 of the mill guide tool 350 can be removed subsequent to mounting the first plate 11. Removal of the mill guide tool 350 can be accomplished by remounting the handle 352 and the shaft 354 of the mill guide tool 350 such that the mill guide tool 350 can be pulled out.

Figure 8A:
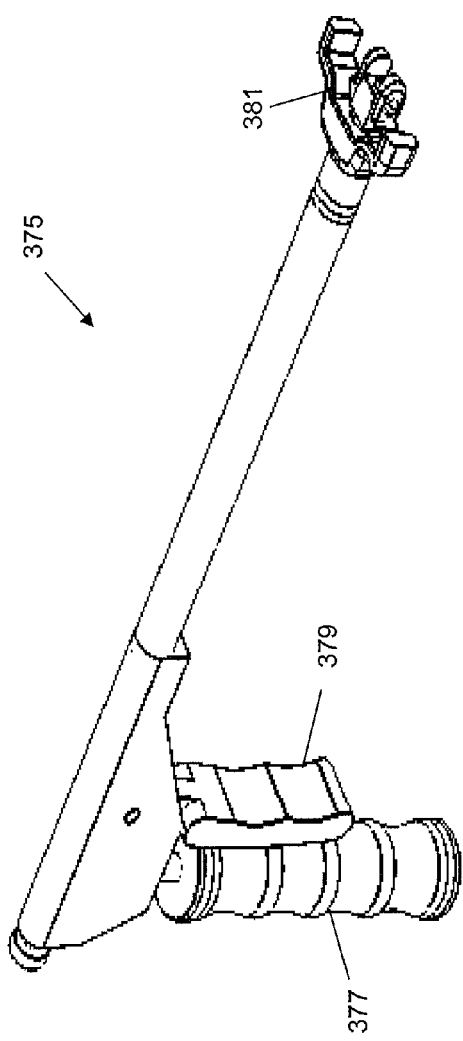
FIG. 8A is a perspective view of a plate insertion tool in accordance with an exemplary embodiment.
Figure 8B:
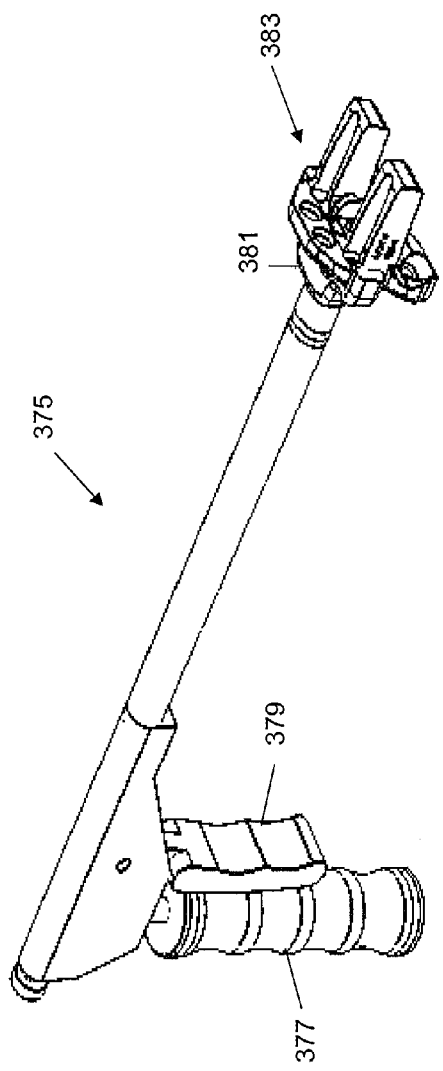
FIG. 8B is a perspective view of a plate insertion tool grabbing a plate in accordance with an exemplary embodiment.

In an exemplary embodiment, the surgeon can use the mounted first plate 11 to align the second plate and the intervertebral body. The second plate may be, for example, any of the second plates described with reference to FIGS. 1A-1C. The second plate and/or the intervertebral body to be used can be selected to optimally fit the patient upon which surgery is being performed. FIG. 8A is a perspective view of a plate insertion tool 375 in accordance with an exemplary embodiment. The plate insertion tool 375 includes a handle 377, a trigger 379, and a plate grabber 381. The surgeon can use the plate insertion tool 375 to place a second plate, an intervertebral body, and/or a stabilization plate in between adjacent vertebral bodies. In an exemplary embodiment, the surgeon can squeeze the trigger 379 to activate the plate grabber 381 such that a plate can be picked up by the plate insertion tool 375. FIG. 8B is a perspective view of the plate insertion tool 375 grabbing a plate and intervertebral body 383 in accordance with an exemplary embodiment. The surgeon can place the plate and intervertebral body 383 in a desired location and squeeze the trigger 379 a second time to release the plate and intervertebral body 383. As such, the surgeon can place the plate and intervertebral body 383 in a location which may be inaccessible to the surgeon's hands. In an alternative embodiment, the surgeon may not use the plate insertion tool to insert the plate and intervertebral body. Additionally, the plate insertion tool 375 can be used to remove the plate and intervertebral body 383.

Figure 9:
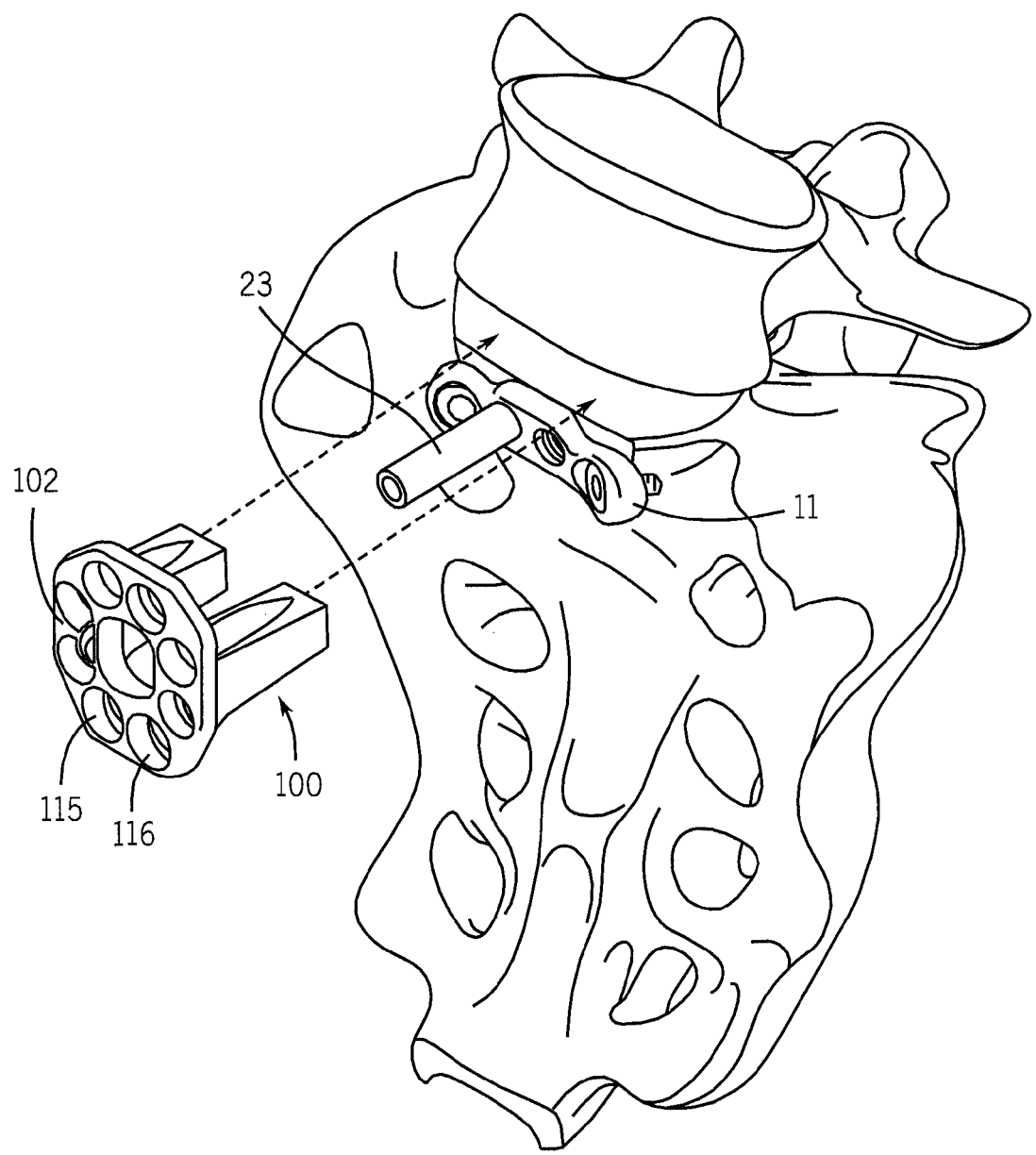
FIG. 9 is a front perspective view illustrating placement of the second plate in accordance with an exemplary embodiment.
Figure 11:
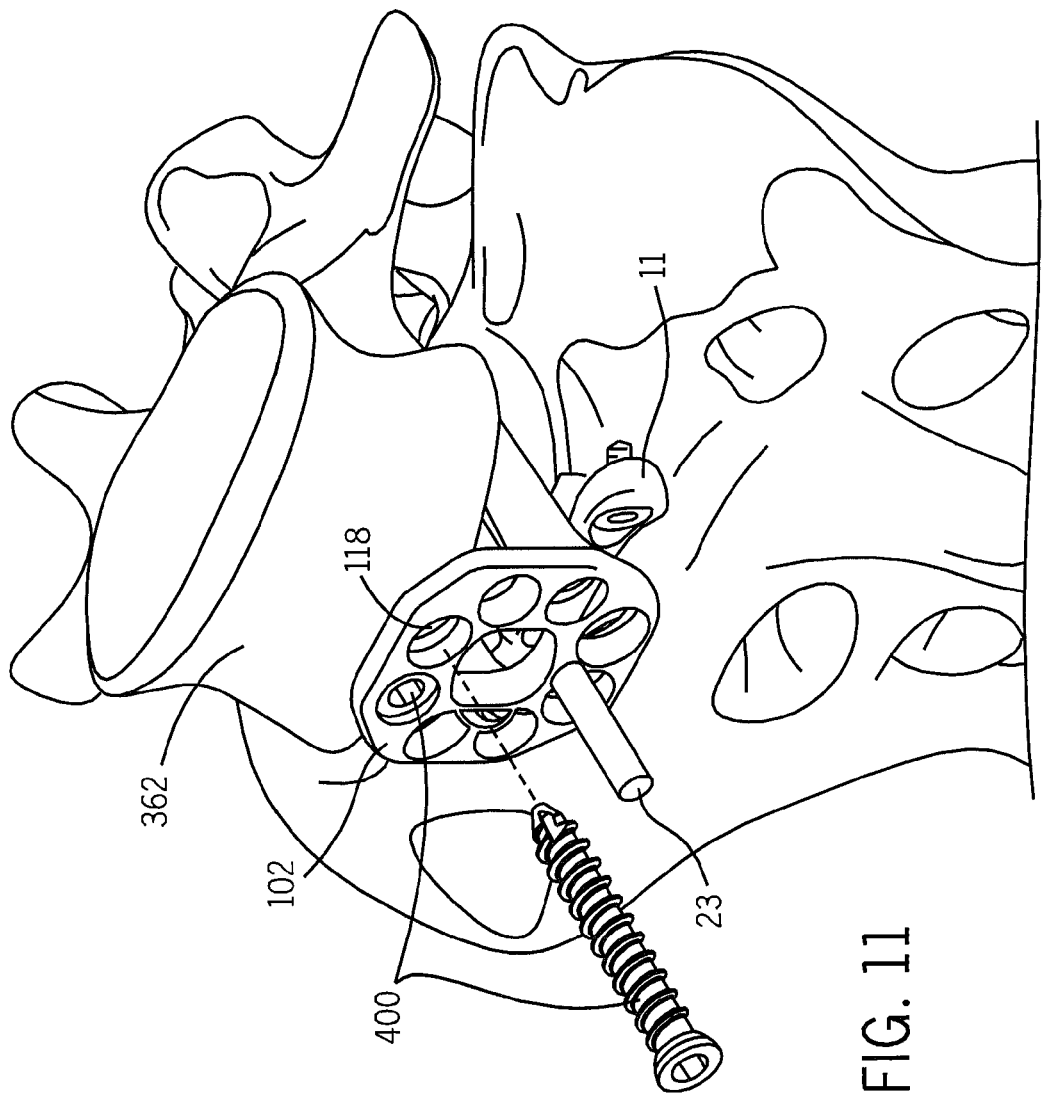
FIG. 11 is a front perspective view illustrating mounting of the second plate in accordance with an exemplary embodiment.

In an exemplary embodiment, the surgeon can begin mounting the second plate by mounting the alignment pin 23 described with reference to FIG. 2B to the first plate 11. FIG. 9 is a perspective view illustrating the alignment pin 23 mounted to the first plate 11 in accordance with an exemplary embodiment. In an alternative embodiment, the surgeon can mount both of the alignment pins 23 and 81 to the first plate 11 such that the second plate 102 can be aligned. FIG. 9 also illustrates the second plate 102 prior to being mounted to the first plate 11. In an exemplary embodiment, the surgeon can position the second plate 102 such that the reduction slot 115 of the second plate 102 is able to receive the alignment pin 23 of the first plate 11. In an alternative embodiment in which alignment pin 81 is also mounted to the first plate 11, the surgeon can position the second plate 102 such that the reduction slot 116 of the second plate 102 is able to receive the alignment pin 81. The second plate 102 can also be positioned such that the intervertebral body 100 mounted to the second plate 102 is properly positioned between the adjacent vertebral bodies. FIG. 10 is a side view illustrating the second plate 102 aligned with the first plate 11 in accordance with an exemplary embodiment. Once the second plate 102 is properly aligned, the surgeon can mount the second plate 102 with fixation members. FIG. 11 is a perspective view illustrating the second plate 102 being mounted to the L-5 vertebra 362 in accordance with an exemplary embodiment. Fixation members 400 can be inserted through the through holes 118 to secure the second plate 102 to the L-5 vertebra 362. In an exemplary embodiment, the fixation members 400 can be inserted to provide unicorticle purchase into the body of the L-5 vertebra 362. Alternatively, the fixation members can be inserted to provide bicorticle purchase in the L-5 vertebra. In another exemplary embodiment, the fixation members 400 can be the same as the fixation members used to mount the first plate 11. Alternatively, a different type and/or size of fixation member can be used to mount the second plate 102.

Figure 12:
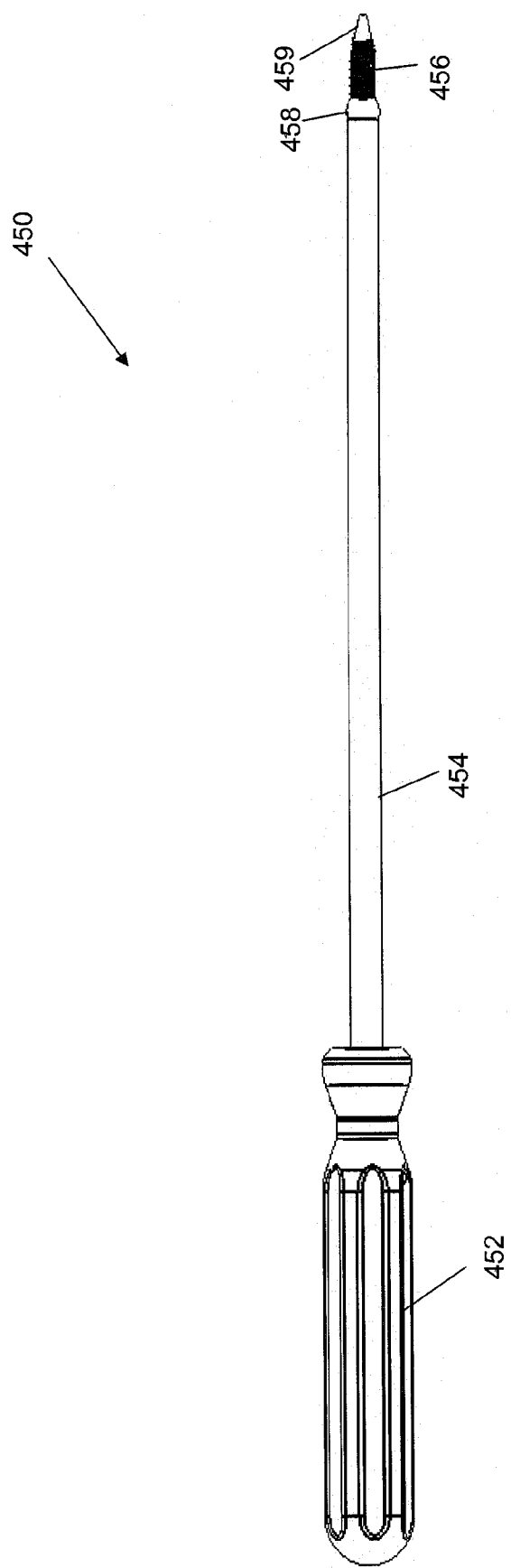
FIG. 12 is a side view illustrating a reduction tool in accordance with an exemplary embodiment.

Once the first plate 11 and the second plate 102 are mounted to adjacent vertebral bodies, the surgeon can correct the misaligned vertebral body using an adjustable connector. FIG. 12 illustrates an adjustable connector that is part of a reduction tool 450 in accordance with an exemplary embodiment. The reduction tool 450 includes a handle 452, a shaft 454, a threaded shaft 456, a tip 459, and a shaft head 458. In an exemplary embodiment, the reduction tool 450 can be inserted into either of the reduction slots 115 and 116 of the second plate 102 and used to translate the first plate 11 and the second plate 102 toward one another, thereby reducing the misalignment. The shaft head 458 can be sized such that only the threaded shaft 456 and the tip 459 of the reduction tool 450 are able to pass through the reduction slots 115 and 116 of the second plate 102. As such, the surgeon can use the handle 452 of the reduction tool 450 to thread the threaded end 456 into either of the guide holes 21 and 80 of the first plate 11. The shaft head 458 can rest within either of the reduction slots 115 and 116 of the second plate 102, and the surgeon can reduce the misalignment by continuing to turn the handle 452 of the reduction tool 450. In one embodiment, the plate insertion tool 375 can be maintained and used to resist the cantilevering forces on the second plate during the reduction of the misalignment. In an exemplary embodiment, as the surgeon reduces the misalignment, the tip 459 of the reduction tool 450 can bore into the vertebral body to which the first plate 11 is mounted. In an alternative embodiment, the adjustable connector can take the form of a ratchet mechanism which can be threaded or unthreaded depending on the embodiment. The ratchet mechanism can be secured to the first plate, the second plate, the intervertebral body, and/or one or more vertebral bodies such that the first plate and the second plate can be translated toward one another via a ratchet. Alternatively, the adjustable connector can take the form of a clamp mechanism which can be secured to the first plate, the second plate, the intervertebral body, and/or one or more vertebral bodies such that the first plate and the second plate can be translated toward one another. In other alternative embodiments, the adjustable connector can take the form of a pulley or any other mechanism which allows the first plate and the second plate to be translated toward one another.

Figure 13:
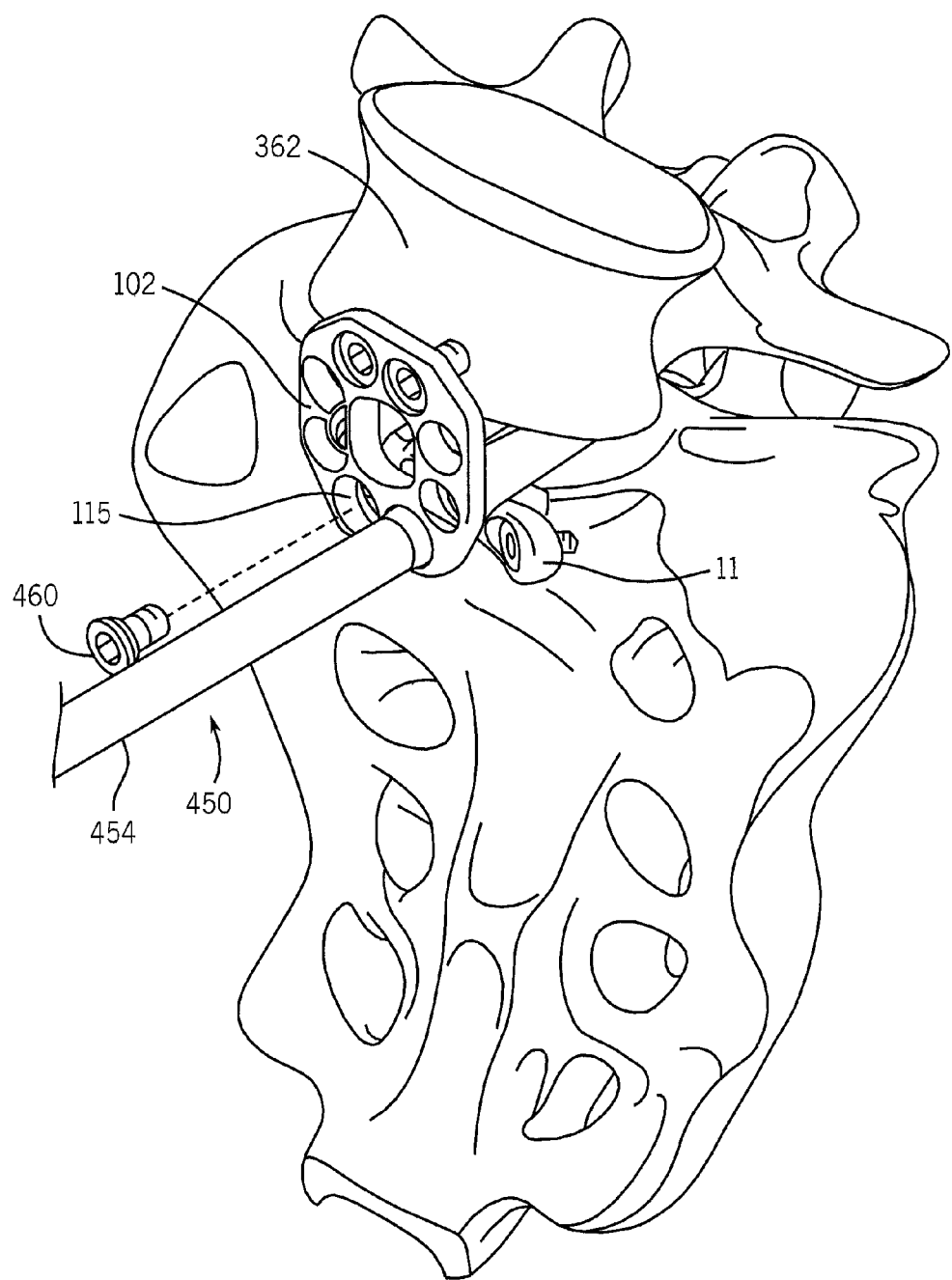
FIG. 13 is a front perspective view illustrating use of the reduction tool in accordance with an exemplary embodiment.

FIG. 13 is a perspective view of the reduction tool 450 being used to reduce a persistent misalignment of the L-5 vertebra 362 in accordance with an exemplary embodiment. During the reduction, the anterior/posterior (or sagittal) distance between the first and second plates is reduced. The sagittal distance can refer to the distance between the front face of the first plate and the back face of the second plate. Thus, the sagittal distance should be understood to mean a distance along an anterior/posterior direction, rather than a superior/inferior direction. In an exemplary embodiment, once the misalignment is reduced, the surgeon can remove the alignment pin from the reduction slot 115 which is not occupied by the reduction tool 450. The surgeon can insert a plate fastener 460 into the unoccupied reduction slot 115 of the second plate 102 such that the plate fastener 460 can be received by the guide hole 21 of the first plate 11. As such, the plate fastener 460 can be used to secure the second plate 102 to the first plate 11 and maintain the adjacent vertebral bodies in an aligned state. In an exemplary embodiment, the reduction tool 450 can be removed once the first plate fastener 460 is in place, and another plate fastener can be inserted into the reduction slot 116 which was previously occupied by the reduction tool 450. The plate fasteners 460 can be any type of screw, bolt, or other fastener capable of securing the second plate 102 to the first plate 11.

Once the second plate 102 is secured to the first plate 11 and the persistent misalignment is reduced, fixation members can be inserted through the interference holes 111 of the second plate 102. The fixation members can be used to provide additional support for the reduction and stabilization device. The fixation members can also convert the intervertebral body 100 into a threaded device which reduces shear forces across the disc space. In an exemplary embodiment, the fixation members inserted through the interference holes 111 can be positioned such that they engage the bone of a vertebral body. In a preferred embodiment, at least about 25% of the width of the fixation member is in one of the vertebral bodies. In a more preferred embodiment, about 25% to 100% of the width of the fixation members are in one of the vertebral bodies. The fixation members can be made of titanium, stainless steel, ceramics, composite materials, or any other material(s) capable of providing purchase into a vertebral body. In an exemplary embodiment, the fixation members inserted through the interference holes 111 can be the same as the fixation members used to mount the second plate to the second vertebral body. Alternatively, different fixation members can be used. In another exemplary embodiment, the locking plate 150 described with reference to FIGS. 3A, 3B, and 4 can be mounted to the second plate 102 such that the fixation members and the plate fasteners are prevented from backing out of the second plate 102. In another exemplary embodiment, the fixation members 51 and 53 of the first plate 11 are prevented from backing out by the second plate 102. Once the spinal column has been appropriately treated, the surgeon can complete the anterior surgery, including placement of fusion-inducing material such as a bone graft or bone morphogenic protein through space 120, using well known surgical techniques.

Figure 14A:
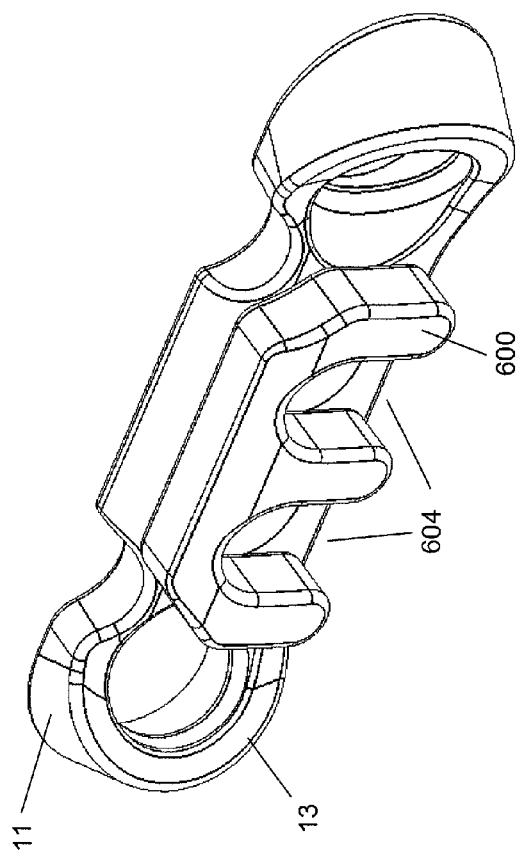
FIG. 14A is a front perspective view of a gap insert in accordance with a first exemplary embodiment.
Figure 14B:
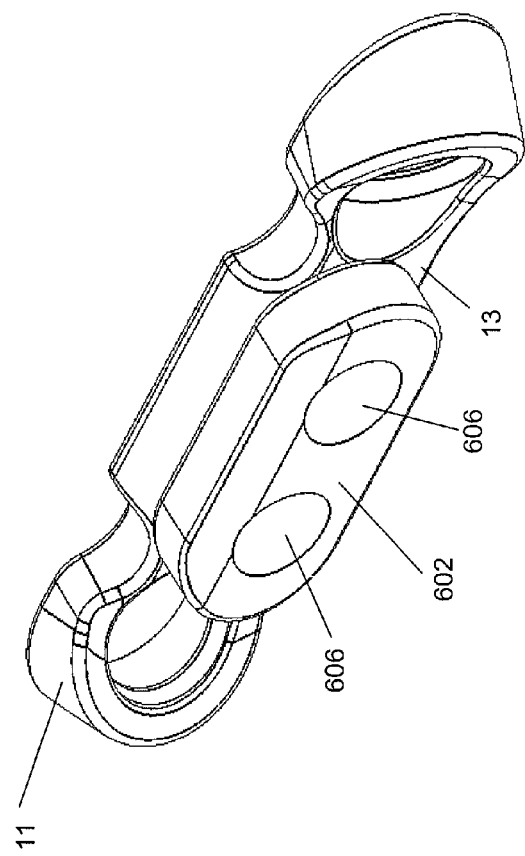
FIG. 14B is a front perspective view of a gap insert in accordance with a second exemplary embodiment.

There may be cases in which the surgeon is unable to reduce a persistent misalignment without causing further injury to the patient. There may also be cases in which the surgeon is only able to partially reduce a persistent misalignment. In such cases, there may be an undesirable gap between the first plate and the second plate. To increase stability of the reduction and stabilization device, the surgeon can use a grommet, wafer, or any other insert capable of being placed in the gap between the first plate and the second plate. FIG. 14A is a perspective view of a gap insert 600 in accordance with a first exemplary embodiment. FIG. 14B is a perspective view of a gap insert 602 in accordance with a second exemplary embodiment. The gap inserts 600 and 602 can be placed between the front face 13 of the first plate 11 and the back face of the second plate (not shown) to eliminate the gap. In addition, the gap insert 600 has apertures 604 and the gap insert 602 has apertures 606 such that plate fasteners can still be used to secure the second plate to the first plate 11. In an exemplary embodiment, the gap inserts 600 and 602 can come in different sizes such that a gap of any size can be filled. Alternatively, the surgeon can use a plurality of gap inserts stacked on one another to fill the gap. In another alternative embodiment, there can be a separate gap insert for each reduction slot. Further, the gap insert(s) can be any other size and/or shape capable of filling the gap while allowing the second plate to be secured to the first plate. In another alternative embodiment, the first plate and/or the second plate can come in various widths such that a full reduction is not achieved for patients in which the full reduction may cause further injury.

Figure 15A:
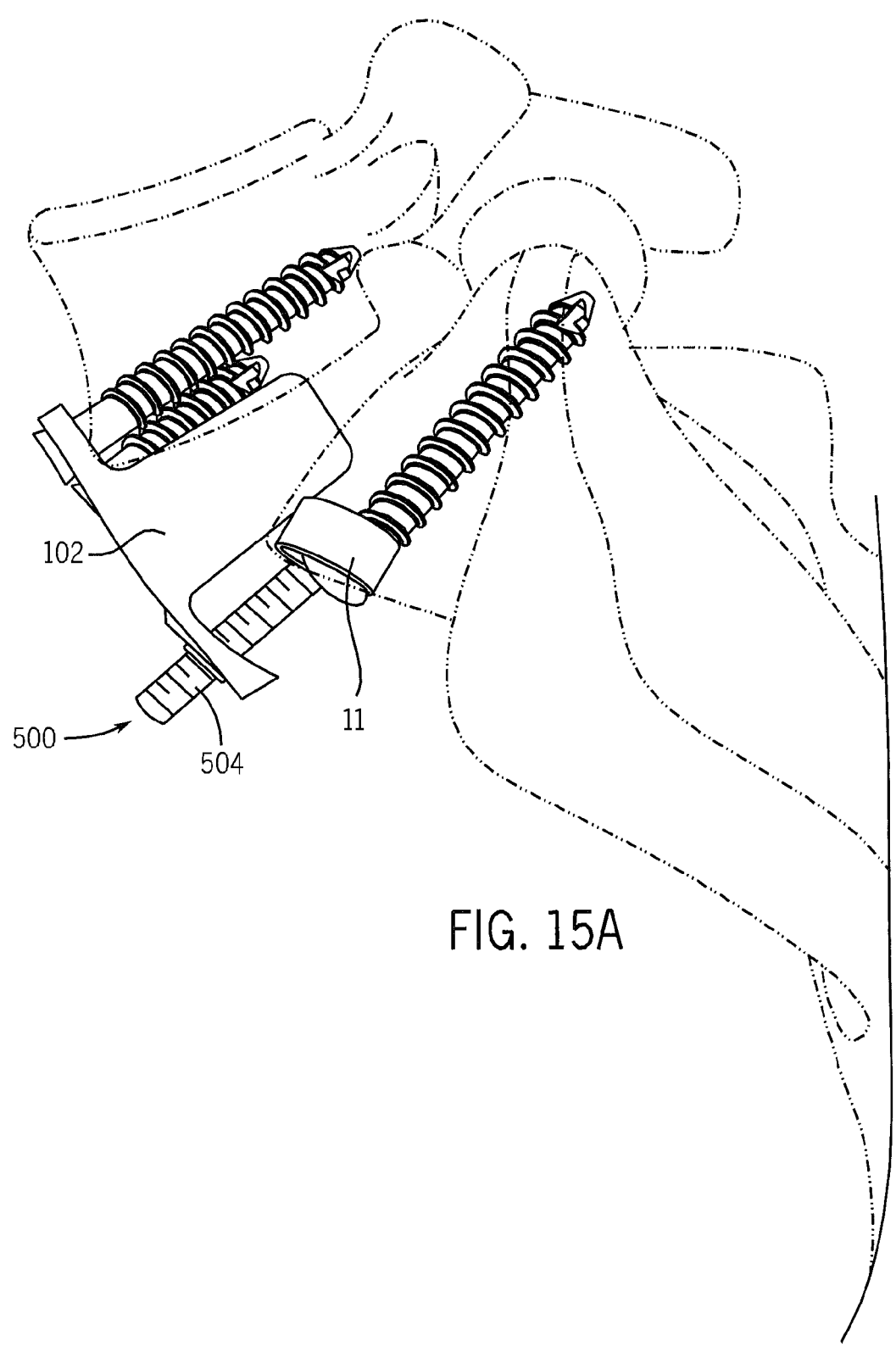
FIG. 15A-C are side views illustrating the use of threaded stems as an adjustable connector in accordance with an exemplary embodiment.
Figure 15B:
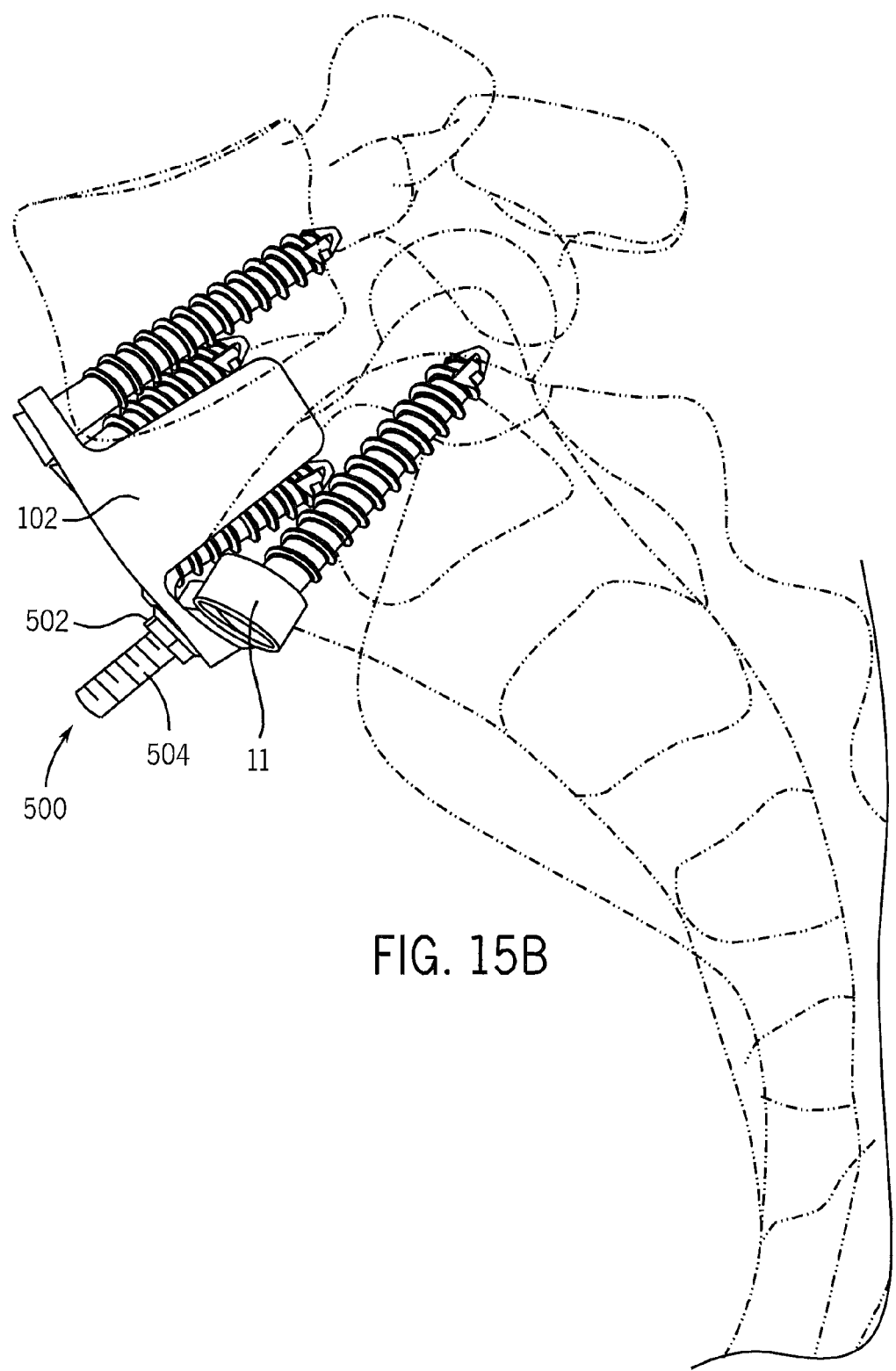
Figure 15C:
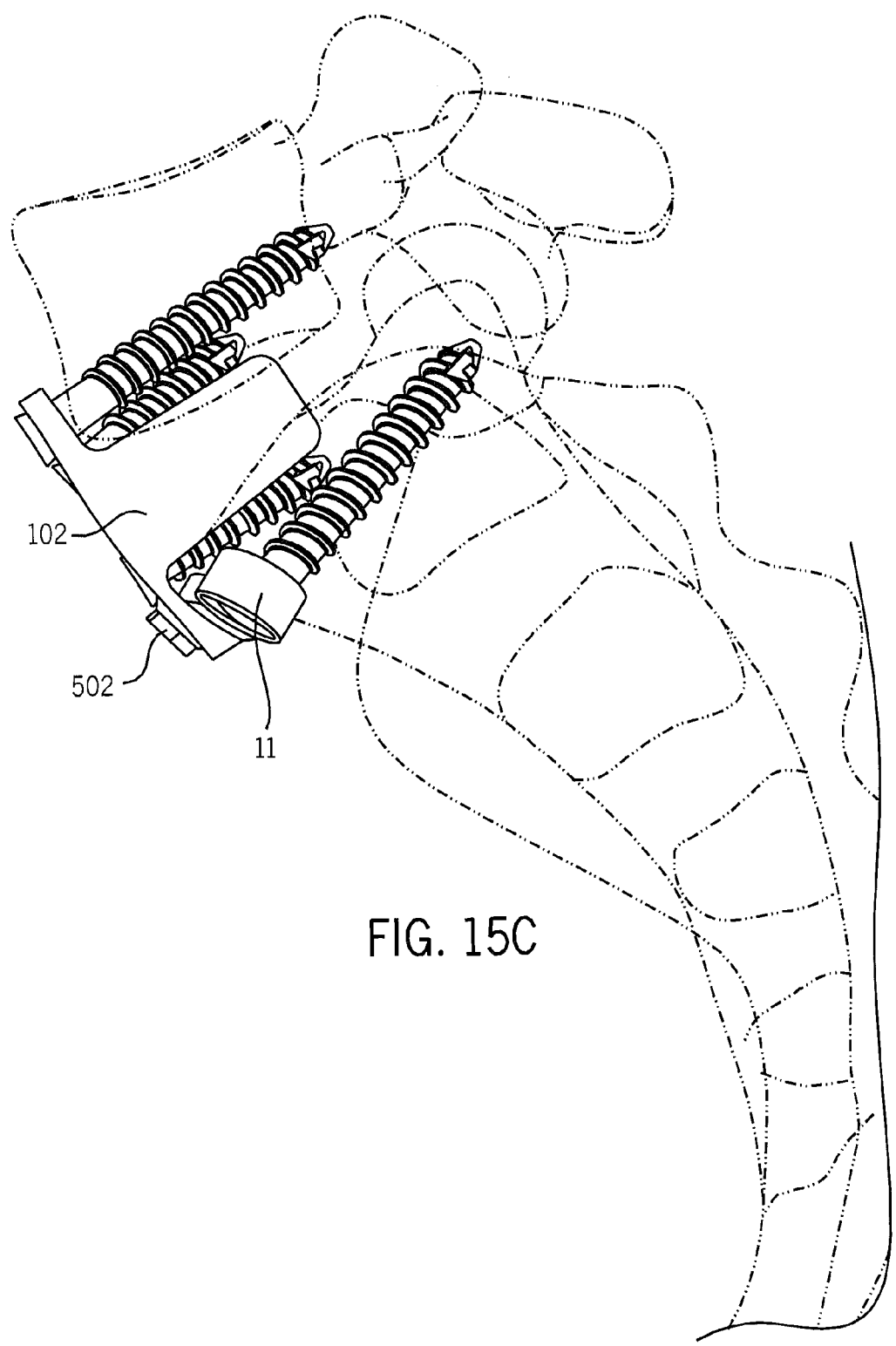

FIGS. 15A-15C illustrate a method for reducing a persistently misaligned vertebral body using a reduction and stabilization device having a different adjustable connector than that of the device depicted in FIGS. 12 and 13. In the embodiment depicted in FIGS. 15A-15C, the adjustable connector includes at least one, and desirably at least two, threaded stems 504 extending outwardly from the front face of first plate 11. Here, the threaded stems are fixed (e.g., welded) to the front face. However, the threaded stems could also be detachable from the front face. At least a portion of the threaded stems 504 can be threaded and capable of receiving a nut or other fastening mechanism. Reduction slots 115 and 116 in the second plate 102 can receive the threaded stems 504 such that the second plate 102 can be aligned and mounted in an optimal location. FIG. 15B is a side view illustrating nuts 502 threaded onto the threaded stems 504. In the illustrative method depicted in FIGS. 15A-15C, fixation of the first plate is accomplished by inserting two bone screws through the through holes in the first plate and into the sacrum. The bone screws may be placed with the assistance of fluoroscopy and may be either unicortical or bicortical in purchase. In a preferred arrangement, the bone screws are placed bicortically to maximize purchase. The surgeon then selects an appropriate second plate 102 and intervertebral body and inserts the intervertebral body between the adjacent vertebral bodies such that the intervertebral extension (e.g., legs) extends in a direction between anterior and posterior. The second plate 102 is positioned such that the threaded stems 504 of the adjustable connector extend through reduction slots in the second plate. The surgeon may then secure the second plate 102 to the second vertebral body. In the illustrative method depicted in FIGS. 15A-15C, this is accomplished by inserting bone screws and interference screws through the through holes in the second plate and into the vertebral body.

Once first plate 11, second plate 102 and the intervertebral body are secured to the adjacent vertebral bodies, nuts 502 are screwed over threaded stems 504 and tightened against the front face of second plate 102. As nuts 502 are tightened, first plate 11 is translated toward second plate 102, thereby reducing the first vertebral body to which first plate 11 is fixed, and bringing it into proper alignment with the second vertebral body. In this manner, a spondylolisthesis may be reduced. During the reduction, the anterior/posterior (or sagittal) distance between the first and second plates is reduced, as shown in FIGS. 15A-15C. The sagittal distance can refer to the distance between the front face of a mounted first plate and the back face of a mounted second plate. Thus, the sagittal distance should be understood to mean a distance along an anterior/posterior direction, rather than a superior/inferior direction. Once the reduction is complete, additional fixation members, such as screws, may be inserted through the through holes in the second plate to fix second plate 102 to the first vertebral body. Finally, the portions of threaded stems 504 extending beyond nuts 502 may be removed. In an exemplary embodiment, the threaded stems 504 can have one or more pre-stressed fractures at which the threaded stems 504 can be broken off. Alternatively, the threaded stems may be screwed into first plate 11 and removed (i.e., unscrewed) after second plate 102 has been fixed to the first vertebral body. As shown in FIG. 15C, the reduction may bring the front face of first plate 11 into contact with the back face of second plate 102, thereby buttressing the bone screws and preventing them from backing out of the vertebral body. Optionally, a locking plate (not shown) may be disposed over the front face of second plate 102 to prevent the other screws from backing out.

In an alternative embodiment, the surgeon may use the reduction and stabilization device without a first plate. Instead of the first plate, the surgeon can use threaded stems mounted to bone screws to guide the second plate and reduce the persistent misalignment. The bone screws can be screwed into a first vertebral body such that the threaded stems extend outwardly from the first vertebral body. A tip of a screwdriver or other tool can be inserted into heads of the bone screws such that the bone screws can be screwed in. In an exemplary embodiment, the heads of the bone screws can be at the ends of the threaded stems such that the bone screws and the threaded stems are a one-piece unit. Alternatively, the threaded stems can be mounted to the heads of the bone screws after the bone screws are screwed into the first vertebral body. The threaded stems extending outwardly from the first vertebral body can be received by the reduction slots of the second plate such that the second plate can be optimally positioned relative to a second vertebral body. The second plate can be mounted to the second vertebral body as described with reference to FIGS. 8-11. The surgeon can also place nuts or other fastening mechanisms onto the threaded stems to reduce the persistent misalignment and stabilize the first vertebral body and the second vertebral body.

For the purposes of this disclosure and unless otherwise specified, "a" or "an" means "one or more." Further, all patents, applications, references and publications cited herein are incorporated by reference in their entirety to the same extent as if they were individually incorporated by reference. The foregoing description of exemplary embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A reduction and stabilization device comprising:
   (a) an intervertebral body configured to be positioned between a first vertebral body and a second vertebral body adjacent to the first vertebral body;
   (b) a first plate configured to be mounted to the first vertebral body such that a rear surface of the first plate is in contact with the first vertebral body;
   (c) a second plate mounted to the intervertebral body, and configured to be mounted to the second vertebral body such that a rear surface of the second plate is in contact with the second vertebral body; and
   (d) an adjustable connector configured to connect the first plate and the second plate in a manner that allows for an adjustment of a sagittal distance between the first and second plates when the device is mounted to the first and second vertebral bodies, wherein the sagittal distance is a distance between a first plane that contains the rear surface of the first plate and a second plane that contains the rear surface of the second plate, and wherein the first plane and the second plane are substantially parallel to a spinal column that includes the first vertebral body and the second vertebral body.

2. The device of claim 1, wherein the first plate defines at least one guide hole configured to receive an alignment pin, and wherein the second plate defines at least one reduction slot configured to receive the alignment pin.

3. The device of claim 2, wherein the adjustable connector comprises a threaded shaft having a shaft head at its distal end, wherein the sagittal distance between the first plate and the second plates is adjusted by inserting the threaded shaft through the at least one reduction slot until the shaft head presses against the second plate and threading the threaded shaft into the at least one guide hole.

4. The device of claim 3, wherein the adjustable connector further comprises a shaft connected to the shaft head, and a handle connected to the shaft.

5. The device of claim 1, wherein the adjustable connector comprises at least one threaded stem extending outwardly from a front face of the first plate and a nut configured to receive the threaded stem, and further wherein the second plate defines at least one reduction slot configured to receive the at least one threaded stem.

6. The device of claim 1, wherein the intervertebral body comprises an intervertebral extension comprising at least two legs which define a U shape as viewed superior to inferior.

7. The device of claim 1, wherein the intervertebral body comprises an intervertebral extension comprising a ring, a disc, a cylinder, or a hollow cage.

8. The device of claim 1, wherein the second plate defines at least one through hole configured to receive a fixation member for mounting the second plate to the second vertebral body and at least one through hole configured to receive a fixation member for mounting the second plate to at least one of the first vertebral body and the first plate.

9. The device of claim 8, further comprising a locking plate configured to be mounted to a front face of the second plate, wherein at least a portion of the locking plate is positioned to cover at least a portion of at least one of the through holes.

10. A method of reducing and stabilizing adjacent vertebral bodies in a patient having a misaligned vertebra using the device of claim 1, the method comprising:
    (a) mounting the first plate to the first vertebral body such that the rear surface of the first plate is in contact with the first vertebral body;
    (b) inserting the intervertebral body between the first vertebral body and the second vertebral body which is adjacent to the first vertebral body;
    (c) mounting the second plate to the second vertebral body such that the rear surface of the second plate is in contact with the second vertebral body; and
    (d) adjusting the sagittal distance between the first plate and the second plate such that a misalignment of the first vertebral body or the second vertebral body is corrected, wherein the sagittal distance is a distance between a first plane that contains the rear surface of the first plate and a second plane that contains the rear surface of the second plate, and wherein the first plane and the second plane are substantially parallel to a spinal column that includes the first vertebral body and the second vertebral body.

11. The method of claim 10, further comprising rigidly fixing the second plate to at least one of the first vertebral body and the first plate after the misalignment has been corrected.

12. The method of claim 11, further comprising removing the adjustable connector.

13. The method of claim 10, wherein the first plate defines at least one guide hole, the second plate defines at least one reduction slot, and the adjustable connector comprises a threaded shaft having a shaft head at its distal end, wherein the sagittal distance between the first plate and the second plates is adjusted by inserting the threaded shaft through the at least one reduction slot until the shaft head presses against the second plate, and threading the threaded shaft into the at least one guide hole.

14. The method of claim 10, wherein the adjustable connector comprises at least one threaded stem extending outwardly from a front face of the first plate and a nut configured to receive the threaded stem, and the second plate defines at least one reduction slot, and further wherein the sagittal distance between the first plate and the second plates is adjusted by inserting the at least one threaded stem through the at least one reduction slot, screwing the nut onto the threaded stem, and tightening the nut against the second plate.

15. The method of claim 10, further comprising shaping an area of the first vertebral body prior to mounting the first plate on the shaped area.

16. A method of shaping a vertebral body using a mill guide tool, the method comprising:
    (a) inserting a wedge between a first vertebral body and a second vertebral body such that a mill guide rests against a side of the first vertebral body, wherein the wedge is configured to maintain a spacing between the first vertebral body and the second vertebral body which is adjacent to the first vertebral body, wherein the mill guide is configured to receive both a cutting end of a milling tool and a plate configured to be mounted to the first vertebral body, wherein the mill guide is sized so that the plate fits within the mill guide such that the mill guide is used to align the plate for mounting to the first vertebral body, and wherein the mill guide is coupled to the wedge in a position such that the mill guide rests entirely against the side of the first vertebral body when the wedge is inserted between the first and second vertebral bodies;
    (b) inserting the milling tool into the mill guide; and
    (c) using the mill guide as a shaping guide to shape the first vertebral body with the milling tool.

17. A reduction and stabilization device comprising:
    (a) an intervertebral body configured to be positioned between a first vertebral body and a second vertebral body adjacent to the first vertebral body;
    (b) a second plate mounted to the intervertebral body, and configured to be mounted to the second vertebral body such that a rear surface of the second plate is in contact with the second vertebral body; and
    (c) one or more threaded stems configured to be mounted to a rear surface of the first vertebral body, wherein the one or more threaded stems are configured to be used to adjust a sagittal distance between the first vertebral body and the second plate when the second plate is mounted to the second vertebral body, wherein the sagittal distance is a distance between a first plane that contains the rear surface of the second plate and a second plane that contains at least a portion of the rear surface of the first vertebral body, and wherein the first plane and the second plane are substantially parallel to a spinal column that includes the first vertebral body and the second vertebral body.

18. The reduction and stabilization device of claim 17, wherein each of the one or more threaded stems is mounted to a screw which is configured to be inserted into the first vertebral body.

* * * * *

UNITED STATES PATENT AND TRADEMARK OFFICE
CERTIFICATE OF CORRECTION

| | |
|---|---|
| PATENT NO. | : 8,430,929 B2 |
| APPLICATION NO. | : 11/621834 |
| DATED | : April 30, 2013 |
| INVENTOR(S) | : Tribus |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1285 days.

Signed and Sealed this
Thirtieth Day of December, 2014

Michelle K. Lee
*Deputy Director of the United States Patent and Trademark Office*